(12) United States Patent
Call et al.

(10) Patent No.: US 10,065,025 B2
(45) Date of Patent: Sep. 4, 2018

(54) OVER-THE-NEEDLE GUIDEWIRE VASCULAR ACCESS SYSTEMS AND METHODS

(71) Applicant: Arizona Medical Systems, LLC, Phoenix, AZ (US)

(72) Inventors: Aaron M. Call, Phoenix, AZ (US); Kelvin Ning, Phoenix, AZ (US)

(73) Assignee: Arizona Medical Systems, LLC, Phoenix, AZ (US)

( * ) Notice: Subject to any disclaimer, the term of this patent is extended or adjusted under 35 U.S.C. 154(b) by 17 days.

(21) Appl. No.: 14/958,661

(22) Filed: Dec. 3, 2015

(65) Prior Publication Data

US 2016/0184557 A1 Jun. 30, 2016

Related U.S. Application Data

(63) Continuation of application No. 14/246,996, filed on Apr. 7, 2014, now Pat. No. 9,205,231.
(Continued)

(51) Int. Cl.
| | |
|---|---|
| *A61M 25/00* | (2006.01) |
| *A61M 25/16* | (2006.01) |
| *A61M 25/09* | (2006.01) |
| *A61M 25/06* | (2006.01) |
| *A61M 39/10* | (2006.01) |

(52) U.S. Cl.
CPC .. *A61M 25/09041* (2013.01); *A61M 25/0606* (2013.01); *A61M 25/09* (2013.01); *A61M 39/10* (2013.01); *A61M 2025/09083* (2013.01); *A61M 2039/1077* (2013.01)

(58) Field of Classification Search
CPC .. A61M 2025/0681; A61M 2025/0687; A61M 2025/018; A61M 25/0662; A61M 25/0606; A61M 2039/1077; A61M 25/09; A61M 25/09041; A61M 2025/09083
See application file for complete search history.

(56) References Cited

U.S. PATENT DOCUMENTS

| 3,863,632 A | 2/1975 | Schwartz |
|---|---|---|
| 5,011,478 A | 4/1991 | Cope |

(Continued)

FOREIGN PATENT DOCUMENTS

| WO | WO 1999/048545 | 9/1999 |
|---|---|---|
| WO | WO 2010/125159 | 11/2010 |

(Continued)

OTHER PUBLICATIONS

Olivetti et al., "Imaging of Urogenital Diseases: A Color Atlas", Springer-Verlag Italia, pp. 482-489 (2008).
(Continued)

*Primary Examiner* — Rebecca E Eisenberg
(74) *Attorney, Agent, or Firm* — Knobbe, Martens, Olson & Bear LLP

(57) ABSTRACT

Systems and methods for accessing body tissue are disclosed. The systems and methods can include an introducer assembly for percutaneous access to a body lumen. The assembly can include a needle and an over-the-needle guidewire. The needle and the guidewire can be inserted into body tissue and the guidewire advanced into the body tissue relative to the needle. The needle can be removed after advancing the guidewire.

4 Claims, 11 Drawing Sheets

Related U.S. Application Data

(60) Provisional application No. 61/892,257, filed on Oct. 17, 2013.

(56) References Cited

U.S. PATENT DOCUMENTS

| | | | |
|---|---|---|---|
| 5,069,674 | A | 12/1991 | Fearnot et al. |
| 5,112,312 | A | 5/1992 | Luther |
| 5,380,290 | A | 1/1995 | Makower et al. |
| 6,235,007 | B1 | 5/2001 | Divino et al. |
| 6,887,249 | B1 | 5/2005 | Houser et al. |
| 7,708,721 | B2 | 5/2010 | Khaw |
| 7,722,567 | B2 | 5/2010 | Tal |
| 8,021,359 | B2 | 9/2011 | Auth et al. |
| 8,485,969 | B2 | 7/2013 | Grayzel et al. |
| 8,882,713 | B1 | 11/2014 | Call et al. |
| 8,945,092 | B1 | 2/2015 | Call et al. |
| 2005/0124845 | A1 | 6/2005 | Thomadsen et al. |
| 2007/0129719 | A1 | 6/2007 | Kendale et al. |
| 2008/0172067 | A1 | 7/2008 | Nita et al. |
| 2009/0187147 | A1 | 7/2009 | Kurth et al. |
| 2010/0292613 | A1* | 11/2010 | Nowak, Jr. .......... A61M 25/09 600/585 |
| 2011/0054487 | A1 | 3/2011 | Farnan |
| 2012/0157854 | A1 | 6/2012 | Kurrus et al. |
| 2012/0197200 | A1 | 8/2012 | Belson |
| 2013/0046203 | A1 | 2/2013 | DeMello |
| 2015/0112310 | A1 | 4/2015 | Call et al. |

FOREIGN PATENT DOCUMENTS

| | | |
|---|---|---|
| WO | WO 2012/125239 | 9/2012 |
| WO | WO 2015/057766 | 4/2015 |

OTHER PUBLICATIONS

Fuller, J.K., "Surgical Technology: Principles and Practice", Elsevier—Health Sciences Division, pp. 836-869 (2012).

Fleming et al., "Toward guidance of epicardial cardiac radiofrequency ablation therapy using optical coherence tomography", Journal of Biomedical Optics, 15(4):041510-1-8 (2010).

GrebSet Micro-introducer Kit, http://vasc.com/wp-content/uploads/2012/01/ML2012-rev-K-GrebSet-and-StraitSet-Brochure.pdf, Vascular Solutions, Inc., (2012).

Comparison of Two Needle Insertion Techniques on Success Rate and Complications During Central Venous Catheterization, http://clinicaltrials.gov/ct2/show/NCT01902355, U.S. National Institutes of Health, date accessed May 6, 2014.

International Search Report and Written Opinion issued in PCT/US2014/060582 dated Feb. 5, 2015, 7 pages.

* cited by examiner

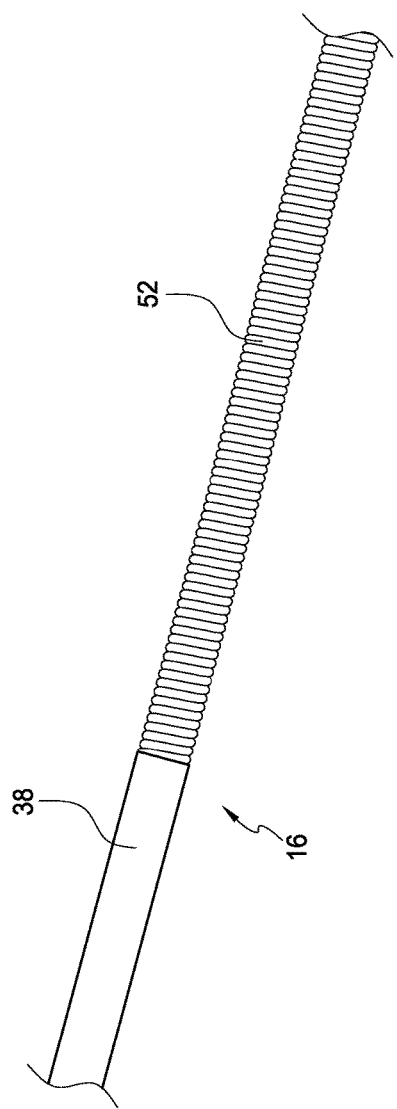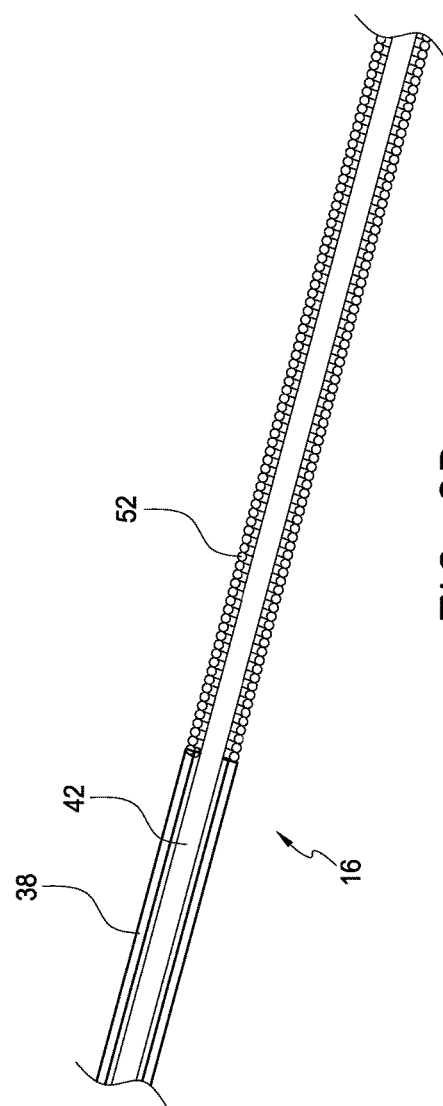
FIG. 9A
FIG. 9B

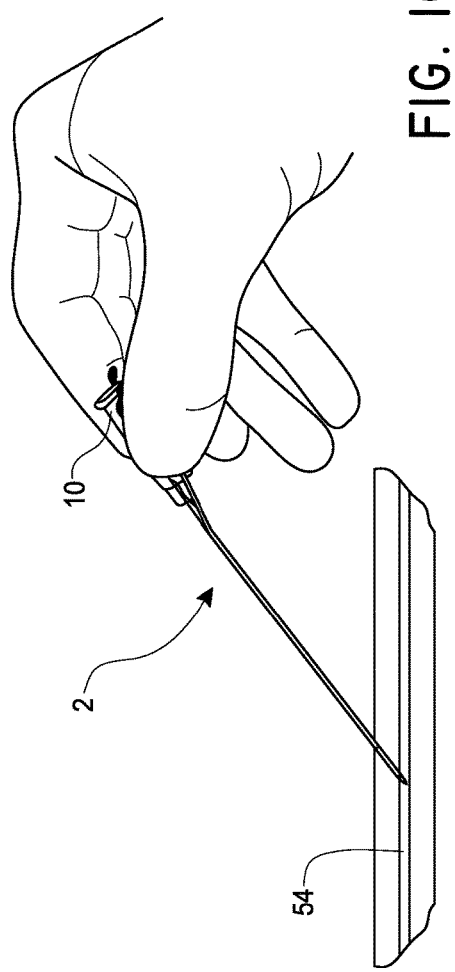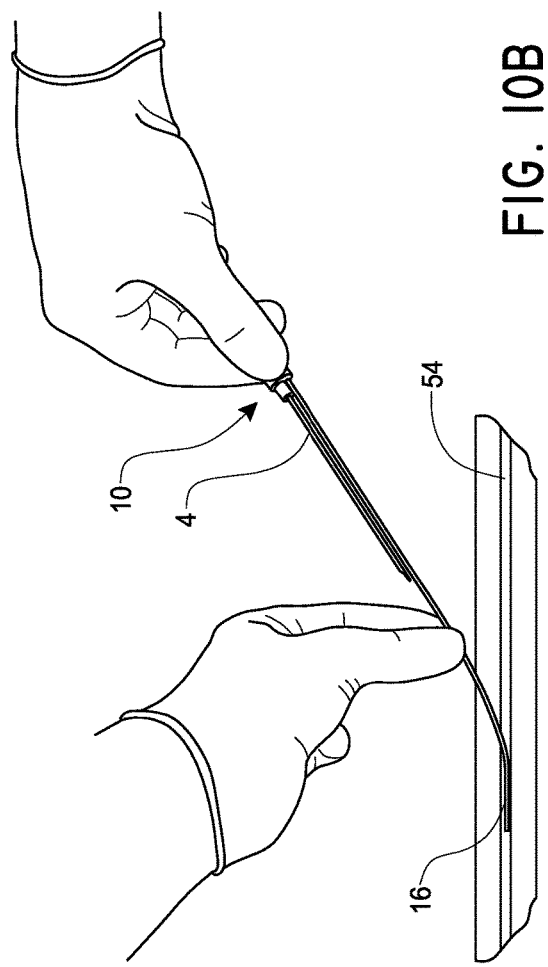

OVER-THE-NEEDLE GUIDEWIRE VASCULAR ACCESS SYSTEMS AND METHODS

CROSS-REFERENCE TO RELATED APPLICATIONS

This application is a continuation of U.S. patent application Ser. No. 14/246,996, titled OVER-THE-NEEDLE VASCULAR ACCESS GUIDEWIRE, and filed Apr. 7, 2014, which claims the benefit under 35 U.S.C. § 119(e) as a nonprovisional of U.S. Provisional Application No. 61/892,257, titled TROCAR SHEATH INTRODUCER KIT, and filed Oct. 17, 2013, the entirety of each of which is incorporated herein by reference.

BACKGROUND

Field

The present application generally relates to providing access to living body tissue, and in particular, to medical access devices provide access to living body tissue, including blood vessels.

Description of the Related Art

Many medical procedures require percutaneous placement of an interventional medical device, such as a catheter, into a body lumen such as an artery or vein. Such interventional medical devices may be used for, among other things, blood pressure monitoring, blood sampling, establishing access for a diagnostic and/or interventional procedure, and administering fluids and medicaments to a patient. In one aspect, percutaneous access to a patient's central venous system is an important aspect of administering intravenous therapy. It is desirable that the therapy be administered in the superior vena cava of the central venous system. In order to gain access, introducer devices are commonly used, through which other medical devices, such as a central venous catheter (CVC), are inserted. One such example of a CVC is a peripherally inserted central catheter (PICC). A PICC typically has one or more tubes, which are externally accessible by a clinician, that converge into a single catheter body that is internally implanted in a vein of the patient. The tubes are adapted to receive medicaments, which are then released through a distal tip of the catheter body into the central venous system of the patient.

In general, percutaneous techniques involve placing a needle through the skin and into a blood vessel, such as an artery or vein, until bleedback is achieved. This is followed by introduction of a flexible introducer guidewire to define the pathway through the skin and into the passageway or lumen of the blood vessel. The needle is then exchanged for an introducer sheath with dilator, which are concentric tubes that are advanced over the introducer guidewire and into the blood vessel. The introducer guidewire and dilator are removed, and exchanged for a catheter or other medical device to be used to deliver medication, and/or implantation of a medical implant such as a filter or a stent into the blood vessel through the introducer sheath.

The purpose of an introducer set is to place a section of tubing, for example an introducer sheath for a catheter, into a vessel, or other body part, that has a sufficiently large and rigid inner diameter to facilitate insertion of other proportionately large tubes, catheters, or other instruments into said vessel or body part. An introducer set commonly contains a small diameter device with a sharp tip, commonly a hypodermic needle, so that the introduction can start with a relatively small, easily produced, puncture wound, minimizing trauma to the involved tissues. This small puncture wound is then expanded, ideally by stretching rather than tearing or cutting the involved tissues, with a tapered dilator. The wall thickness of the introducer sheath is in some embodiments as small as possible, minimizing the outside diameter of the introducer sheath to minimize the trauma to the body tissues involved while maximizing the size of the inside of the opening for insertion of other devices.

Described is a procedure for preparing an opening to introduce devices into a blood vessel, a body opening, or other body duct is a multi-step procedure involving a number of independent devices and steps. The following steps set forth a conventional introducer set and method of use.

First, a hypodermic needle with glass or clear or translucent plastic syringe attached, is inserted into a vessel. When the pressure in the syringe is lower than the pressure in the vessel, blood will flow up the needle and into the syringe where it can be observed by the operator. Observed features, such as color and rate of flow of blood, confirm that a blood vessel has been hit, and indicate the type of vessel. The ability to observe the blood is a necessary part of the procedure for blood vessel access or, for example, access to a cyst or duct.

Second, while holding the needle in place, the syringe is disconnected from the needle. At this point, blood can flow, or squirt, out of the proximal opening of the needle and/or air can be sucked into the needle if the pressure in the body vessel should fall below ambient pressure. This latter effect can occur in a vein during normal inspiration, when the veins often collapse under negative pressure created in the venous system by the depression of the diaphragm.

Third, as quickly as possible, to minimize the above effects, a guidewire is inserted into the proximal end of the needle, effectively and approximately closing the hole and stopping fluid or air flow. The guidewire is then threaded well into the vessel. The guidewire is flexible to turn the corner from the needle-stick track, which enters the vessel at an acute angle.

Fourth, the needle is then removed by pulling the needle backwards over the full length of the guidewire while simultaneously holding the guidewire in place.

Fifth, a dilator with an introducer sheath slidingly positioned over the dilator is threaded onto the proximal end of the guidewire. The distal tip of the dilator has an inner diameter just large enough to slip over the guidewire with little friction. The outer diameter of the distal tip of the dilator is only slightly larger than the inner diameter, creating a relatively smooth transition from guidewire to dilator. The outer diameter of the dilator is tapered to a larger dimension, the taper occurring over a distance of about, for example, one or more centimeters back from the tip. The distal tip of the introducer sheath is positioned just proximal to the proximal end of the taper. As the dilator-sheath combination is pushed forward, the tip follows the guidewire into the vessel, and the following tapered outer dimension dilates the hole through the body and the wall of the vessel, stretching the inner diameter of the vessel to a larger than normal diameter. The dilator must also be flexible enough to turn the corner from the needle track to the long axis of the vessel. However, a relatively large force may be required to push the dilator through all the intervening tissues and to expand the vessel diameter, so the dilator/guidewire combination should have a proportionately large stiffness to prevent buckling. The distal end of the introducer sheath follows the dilator into the vessel. This sheath commonly has a constant inner diameter, just big enough to slip over the outer diameter of the dilator, and a constant-thickness thin wall. It should be flexible enough to pass from the body tissues outside the vessel, enter the vessel at an angle, and turn the corner to follow the long axis of the vessel. The force required again may be relatively large, but the dilator prevents buckling of the thin-walled, relatively flexible introducer sheath. Note that it could be difficult to insert the introducer sheath over the guidewire without inserting the dilator first because the required force would be great, the trauma to the tissues would be severe, and the stiffness of such a sheath would be inconsistent with the need for a flexible thin-walled device. Similarly, the size of the guidewire should be taken into consideration depending on the size of the sheath being introduced.

Sixth, the dilator is then withdrawn, holding only the introducer sheath, and perhaps the guidewire, in place. The guidewire can be removed as well. In some cases, the guidewire can be optionally exchanged for a second, larger diameter, stiffer guidewire, and the introducer sheath can be removed. A larger diameter dilator can then be inserted to enlarge the percutaneous opening, and then removed. A larger diameter introducer sheath and/or catheter (e.g., a dialysis catheter) can then be inserted. This introducer sheath permits repeated insertion and removal of useful devices of relatively large diameter, such as infusion catheters, balloon angioplasty catheters, angioscopes, etc. into the body and through the vessel wall without repeated trauma to vessel or intervening tissues. Improved methods and devices of accessing a body lumen are needed.

SUMMARY

The necessary threading of numerous components may require a large sterile field in which to work, can be difficult to perform with just two hands, and often permits increased blood loss during the process. Disclosed herein are systems and methods for reducing the need for multiple threadings/percutaneous dilations, reducing the incidence of needle sticks in some cases (such as when the vessel is not properly cannulated, reducing the number of devices used during the procedure, reducing blood loss, reducing the time required to gain intravascular access, and associated healthcare costs with, for example, the foregoing. Embodiments herein disclose an assembly which can replace the multiple components, each of which must be handled separately in the classical, conventional vascular access procedure, and reduce the number of steps required to gain access. Additionally, embodiments herein disclose an assembly can be used with ease by a single user, whereas conventional methods may generally require more than one person to handle the multiple components.

Disclosed herein and in the figures and tables that follow are systems and methods relating to an over-the-needle guidewire vascular access system and components thereof, which can advantageously be deployed in less steps, and thereby provide more rapid access to, for example, a body lumen, such as an artery or vein for sample collection, infusion, or procedural access (such as a cardiovascular or vascular procedure, including angioplasty, stent placement, valve or other implant placement, and the like). Any dimensions listed in the tables and figures that follow are non-limiting examples, and include the listed quantitative dimensions and quantitative dimensions that are approximately the listed dimensions.

In some embodiments, disclosed are methods of accessing a body lumen, such as a blood vessel for example, including the steps of: puncturing the body lumen with a needle loaded with an over-the-needle wire; advancing the over-the-needle wire into the body lumen; withdrawing the needle while maintaining the wire in position; inserting a sheath/dilator having a diameter greater than that of the over-the-needle wire; and withdrawing the guidewire and dilator, leaving the sheath inside the body lumen. In some embodiments, puncturing the body lumen can be via a percutaneous or cut-down approach. In some embodiments, the method could include, e.g., needle, wire, sheath, and dilator features as described elsewhere herein.

In some embodiments, a vascular access system can include a needle, such as a 24 gauge needle having one or more of a 0.022" OD, 0.012" or 0.014" ID, and a length of about 3.5". The assembly can also include a guidewire having a first, e.g., proximal portion and a second, e.g., distal portion. The distal portion of the guidewire can be sized and configured to be fitted over-the-needle, such as concentrically and/or coaxially over the needle. The distal portion of the guidewire can, in some embodiments, include a lumen, such as a central lumen, configured to house the needle therethrough, and, for example, have a 0.035" OD and/or 0.023" ID, and be about 2" in length (for a 18" total length guidewire). In some embodiments, the distal portion of the guidewire can have a length that is less than about 70%, 60%, 50%, 40%, 30%, 25%, 20%, 15%, 10%, or less with respect to the entire length of the guidewire, or between about 5-30%, about 10-20%, or about 10-15% of the entire length of the guidewire. The distal portion of the guidewire can, in some embodiments, be about 16" to about 18" in total length and/or have a solid core (no central lumen, and thus the distal portion of the guidewire may not be over-the-needle). The guidewire can be made of any appropriate material, such as a metal, such as stainless steel or nitinol. In some embodiments, the first portion of the guidewire could be made of a first material, such as a polymer, while the second portion of the guidewire could be made of a second material different from the first material, such as a metal. In some embodiments, axially in between the first portion of the guidewire and the second portion of the guidewire a needle entrance zone can be present on the guidewire that can be configured to allow the needle to access the central lumen of the guidewire. The needle entrance zone could include, for example, an aperture or slot/skive detail. The dilator-sheath assembly can include an introducer sheath (e.g., a 12 French sheath), and a dilator that can be 0.035" compatible, for example. The introducer sheath can have a central lumen sized and configured to house the over-the-needle guidewire therethrough.

In some embodiments, a vascular access system includes one or more of the following: a needle having a proximal end, a sharpened distal end, a tubular body, and a central lumen therethrough; an over-the-needle guidewire configured to fit over the outside diameter of the needle, the guidewire comprising a first proximal section, a second middle section, and a third distal section; the first proximal section comprises a first cross-sectional profile in the first proximal section; the second middle section comprises an outer tubular sidewall, a skive in the outer tubular sidewall configured for passage of the needle therethrough, the guidewire having the first cross-sectional profile proximally and a second cross-sectional profile distally, and a transition zone between the first cross-sectional profile and the second cross-sectional profile; the second cross-sectional profile is smaller than the first cross-sectional profile; the third distal section comprises the outer tubular sidewall having the second cross-sectional profile; and/or a luer connector operably connected to the needle having at least one input port fluidly connected to the central lumen of the needle, and a guidewire lumen not fluidly connected to the central lumen of the needle, the guidewire lumen configured to slidably house the guidewire therethrough, the guidewire lumen having a longitudinal axis that forms an acute angle with respect to a longitudinal axis of the luer connector.

In some embodiments, the vascular access system can further include one or more of the following: the first proximal section further comprises a coil disposed at least partially over a core wire; the core wire is embedded into the guidewire in at least the third distal section; the core wire at least partially occludes the skive; the coil of the first proximal section comprises a wire circumferentially wound about a central coil axis to form the coil; the wire has an outer diameter of 0.006 inches; the coil formed from the wound wire has an outer diameter of about 0.035 inches; a material of the wire comprises stainless steel; a material of the core wire comprises stainless steel; the longitudinal axis of the luer connector is parallel to a longitudinal axis of the needle; when the guidewire slides through the guidewire lumen, the guidewire in the guidewire lumen is positioned at the acute angle relative to the longitudinal axis of the needle; the acute angle of the guidewire is formed at the skive in the second middle section of the guidewire; the acute angle is between about 5 to 45 degrees; the acute angle is about 15 degrees; the outer tubular wall of the second middle section and the third distal section extends from the skive through the guidewire lumen when the guidewire is positioned over the needle; the guidewire covers a majority of an overall length of the needle when the guidewire is positioned over the needle; an outer diameter of the guidewire tapers substantially to an outer diameter of the needle at the third distal section proximal to the sharpened distal end of the needle; an outer diameter of the needle is about 0.022 inches and an inner diameter of the guidewire at the third distal section is about 0.024 inches; the inner diameter of about 0.024 inches extends through second middle section and the first proximal section; an outer diameter of the guidewire is about 0.035 inches; the first cross-sectional profile of the guidewire in the first proximal section is about 0.015 inches in diameter; a cross-sectional profile of the transition zone of the guidewire between the first cross-sectional profile and the second cross-sectional profile is about 0.010 inches in a dimension of the cross-sectional profile of the transition zone; the cross-sectional profile of the transition zone is round and the dimension of the transition zone is a diameter; a first dimension of the second cross-sectional profile is less than about 0.015 inches; a second dimension of the second cross-sectional profile is about 0.004 inches such that the second cross-sectional profile is substantially rectangular; the skive has an opening length of about 0.060 inches when the needle passes therethrough; the skive has an overall length in the guidewire of about 0.080 inches when the needle passes therethrough; an entirety of a perimeter of the skive formed in guidewire is above a plane passing through a central longitudinal axis of the guidewire; a material of the guidewire comprises a polymer; a material of the second middle section and the third distal section comprises a polymer; the guidewire has an entire length of about 45 centimeters; and/or a combined length of the second middle section and the third distal section is less than about 30% of an entire length of the guidewire.

In some embodiments, a vascular access system includes one or more of the following: a needle having a proximal end, a sharpened distal end, a tubular body, and a central lumen therethrough; an over-the-needle guidewire configured to fit over the outside diameter of the needle, the guidewire comprising a proximal section and a distal section; the proximal section comprises a first cross-sectional profile in the proximal section; the distal section comprises an outer tubular sidewall, a skive in the outer tubular sidewall configured for passage of the needle therethrough, the guidewire having the first cross-sectional profile proximally and a second cross-sectional profile distally, and a transition zone between the first cross-sectional profile and the second cross-sectional profile; the second cross-sectional profile is smaller than the first cross-sectional profile; and/or a luer connector operably connected to the needle having at least one input port fluidly connected to the central lumen of the needle, and a guidewire lumen not fluidly connected to the central lumen of the needle, the guidewire lumen configured to slidably house the guidewire therethrough, the guidewire lumen having a longitudinal axis that forms an acute angle with respect to a longitudinal axis of the luer connector.

In some embodiments, a luer for use with a needle for accessing a body lumen includes one or more of the following: an adapter configured to accept to a needle for penetrating body tissue to provide access to a body lumen; a fluid channel connected to the adapter, the fluid channel configured to fluidly connect to a central lumen of the needle when the needle is in the adapter; a guidewire opening configured to accept a guidewire therethrough, the guidewire configured to be positioned over the needle; the guidewire opening is not in fluid communication with the lumen of the needle; and/or the guidewire opening is configured to position a proximal portion of the guidewire that passes through the guidewire opening at a predetermined angle relative to a distal portion of the guidewire that is positioned over the needle.

In some embodiments, the luer can further include one or more of the following: a longitudinal axis of the fluid channel and a longitudinal axis of the guidewire opening are at the predetermined angle relative to each other; the predetermined angle is between about 5 to 45 degrees; the predetermined angle is about 15 degrees; a hub in fluid communication with the fluid channel, the hub configured to connect to an adapter of a syringe; a longitudinal axis of the hub is parallel a longitudinal axis of the hub; and/or gripping panels on the luer for a user to grip the luer while using the luer; a material of the luer comprises a transparent polymer.

In some embodiments, a luer for use with a needle for accessing a body lumen includes one or more of the following: an adapter configured to accept to a needle for penetrating body tissue to provide access to a body lumen; a fluid channel connected to the adapter, the fluid channel configured to fluidly connect to a central lumen of the needle when the needle is in the adapter; a guidewire opening configured to accept a guidewire therethrough, the guidewire configured to be positioned over the needle; the guidewire opening is not in fluid communication with the lumen of the needle; the guidewire opening is configured to position a proximal portion of the guidewire that passes through the guidewire opening at a predetermined angle relative to a distal portion of the guidewire that is positioned over the needle; and/or the guidewire opening is sized for the guidewire to slide therethrough while the predetermined angle is maintained between a sliding portion of the guidewire in the guidewire opening and at least a part of the distal portion of the guidewire that is over the needle.

In some embodiments, the luer can further include one or more of the following: a longitudinal axis of the fluid channel and a longitudinal axis of the guidewire opening are at the predetermined angle relative to each other; the predetermined angle is between about 5 to 45 degrees; the predetermined angle is about 15 degrees; a hub in fluid communication with the fluid channel, the hub configured to connect to an adapter of a syringe; a longitudinal axis of the hub is parallel a longitudinal axis of the hub; and/or gripping panels on the luer for a user to grip the luer while using the luer; a material of the luer comprises a transparent polymer.

In some embodiments, a luer for use with a needle for accessing a body lumen includes one or more of the following: an adapter configured to accept to a needle for penetrating body tissue to provide access to a body lumen; a fluid channel connected to the adapter, the fluid channel configured to fluidly connect to a central lumen of the needle when the needle is in the adapter; a guidewire opening configured to slidingly accept a guidewire therethrough, the guidewire configured to be positioned over the needle; and/or the guidewire opening is configured to position a proximal portion of the guidewire that passes through the guidewire opening at a predetermined angle relative to a distal portion of the guidewire that is positioned over the needle.

In some embodiments, the luer can further include one or more of the following: a longitudinal axis of the fluid channel and a longitudinal axis of the guidewire opening are at the predetermined angle relative to each other; the predetermined angle is between about 5 to 45 degrees; the predetermined angle is about 15 degrees; a hub in fluid communication with the fluid channel, the hub configured to connect to an adapter of a syringe; a longitudinal axis of the hub is parallel a longitudinal axis of the hub; and/or gripping panels on the luer for a user to grip the luer while using the luer; a material of the luer comprises a transparent polymer.

In some embodiments, a guidewire for use with a needle for accessing a body lumen includes one or more of the following: a first portion comprising a coil and a core wire, the core wire housed within the coil; a second portion distal to the first portion along the guidewire, the second portion comprising the core wire and a tube adjacent to the coil, the tube forming a tube lumen, the core wire housed within the tube lumen, the tube comprising an opening communicating with the tube lumen, the opening positioned in the second portion; the opening is configured to accept a needle therethrough and into the tube lumen; and/or a third portion distal to the second portion along the guidewire, the second portion between the first portion and the third portion, the third portion comprising the core wire and the tube having the tube lumen, the core wire housed within the tube lumen along the third portion and configured to extend adjacent the needle when the needle is inserted into the tube lumen in the third portion.

In some embodiments, the guidewire can further include one or more of the following: the coil comprises a cord that is circumferentially coiled about a central axis shared by the core wire and the coil, the cord that is coiled forming a cord lumen to house the core wire concentrically with the coil; a cross-sectional profile of the core wire becomes smaller in at least one dimension as the core wire extends from the second portion to the third portion; the cross-sectional profile of the core wire is round as the core wire extends from the first portion to the second portion; the cross-sectional profile tapers from about 0.015 inches in diameter to about 0.010 inches in diameter as the core wire extends from the second portion to the third portion; the cross-sectional profile of the core wire tapers to be rectangular in the third portion; the rectangular cross-sectional profile has dimensions of about 0.010 inches by 0.004 inches; an inner diameter of the third portion is about 0.024 inches; the inner diameter of about 0.024 inches extends through second portion and the first portion; an outer diameter of the first, second, and third portions is about 0.035 inches; the core wire in the first portion has a diameter of about 0.015 inches; the core wire is embedded into the guidewire in at least the third portion; the core wire at least partially occludes the opening; the opening has an opening length of about 0.060 inches when the needle is accepted therethrough; the opening has an overall length in the guidewire of about 0.080 inches when the needle is accepted therethrough; an entirety of a perimeter of the opening formed in the guidewire is above a plane passing through a central longitudinal axis of the guidewire; the first portion of the guidewire is configured to intersect the needle at an acute angle when the needle is accepted therethrough; the coil of the first portion comprises a wire circumferentially wound about a central axis to form the coil; the wire has an outer diameter of 0.006 inches; the coil formed from the wound wire has an outer diameter of about 0.035 inches; a material of the wire comprises stainless steel; a material of the guidewire comprises a polymer; a material of the second portion and the third portion comprises a polymer; a material of the core wire comprises stainless steel; the guidewire has an entire length of about 18 inches or 45 centimeters; and/or a combined length of the second portion and the third portion is less than about 30% of an entire length of the guidewire.

In some embodiments, a guidewire for use with a needle for accessing a body lumen includes one or more of the following: a first portion comprising a coil and a core wire, the core wire housed within the coil; a second portion distal to the first portion along the guidewire, the second portion comprising the core wire and a tube adjacent to the coil, the tube forming a tube lumen, the core wire housed within the tube lumen, the tube comprising an opening communicating with the tube lumen, the opening positioned in the second portion; the opening is configured to accept a needle therethrough and into the tube lumen; and/or a third portion distal to the second portion along the guidewire, the second portion between the first portion and the third portion, the third portion comprising the core wire and the tube having the tube lumen, the core wire housed within the tube lumen along the third portion and tapers in cross-sectional profile to abut the needle when the needle is inserted into the tube lumen in the third portion to retain a substantially same diameter of the tube lumen from the second portion to the third portion.

In some embodiments, the guidewire can further include one or more of the following: the coil comprises a cord that is circumferentially coiled about a central axis shared by the core wire and the coil, the cord that is coiled forming a cord lumen to house the core wire concentrically with the coil; a cross-sectional profile of the core wire becomes smaller in at least one dimension as the core wire extends from the second portion to the third portion; the cross-sectional profile of the core wire is round as the core wire extends from the first portion to the second portion; the cross-sectional profile tapers from about 0.015 inches in diameter to about 0.010 inches in diameter as the core wire extends from the second portion to the third portion; the cross-sectional profile of the core wire tapers to be rectangular in the third portion; the rectangular cross-sectional profile has dimensions of about 0.010 inches by 0.004 inches; an inner diameter of the third portion is about 0.024 inches; the inner diameter of about 0.024 inches extends through second portion and the first portion; an outer diameter of the first, second, and third portions is about 0.035 inches; the core wire in the first portion has a diameter of about 0.015 inches; the core wire is embedded into the guidewire in at least the third portion; the core wire at least partially occludes the opening; the opening has an opening length of about 0.060 inches when the needle is accepted therethrough; the opening has an overall length in the guidewire of about 0.080 inches when the needle is accepted therethrough; an entirety of a perimeter of the opening formed in the guidewire is above a plane passing through a central longitudinal axis of the guidewire; the first portion of the guidewire is configured to intersect the needle at an acute angle when the needle is accepted therethrough; the coil of the first portion comprises a wire circumferentially wound about a central axis to form the coil; the wire has an outer diameter of 0.006 inches; the coil formed from the wound wire has an outer diameter of about 0.035 inches; a material of the wire comprises stainless steel; a material of the guidewire comprises a polymer; a material of the second portion and the third portion comprises a polymer; a material of the core wire comprises stainless steel; the guidewire has an entire length of about 18 inches or 45 centimeters; and/or a combined length of the second portion and the third portion is less than about 30% of an entire length of the guidewire.

In some embodiments, a guidewire for use with a needle for accessing a body lumen includes one or more of the following: a first portion comprising a coil and a core wire, the core wire housed within the coil; and/or a second portion distal to the first portion along the guidewire, the second portion comprising the core wire and a tube adjacent to the coil, the tube forming a tube lumen, the core wire housed within the tube lumen, the tube configured to accept a needle therethrough and into the tube lumen with the core wire extending adjacent the needle in the second portion when the needle is inserted into the tube lumen of the second portion.

In some embodiments, a method for accessing a blood vessel with an over-the-needle guidewire includes one or more of the following: puncturing the blood vessel with a needle having an over-the-needle portion of a guidewire disposed on the needle; advancing the over-the-needle portion of the guidewire into the blood vessel while maintaining a position of the needle relative to the blood vessel; the guidewire comprises a proximal portion, the over-the-needle portion, and a support wire; the support wire is housed within a lumen in guidewire, the lumen extending through the proximal portion and the over-the-needle portion of the guidewire; the support wire extends from the proximal portion at least partially into the over-the-needle portion adjacent to the needle within the lumen of the guidewire when the needle is puncturing the blood vessel, the support wire configured to direct advancing forces on the guidewire along the needle while the over-the-needle portion of the guidewire is being advanced into the blood vessel; and/or the needle from the over-the-needle portion of the guidewire while maintaining a position of the advanced guidewire relative to the blood vessel.

In some embodiments, the method for accessing a blood vessel can further include one or more of the following: the guidewire is pushed at an about 15 degree angle relative to a longitudinal axis of the needle when the guidewire is being advanced into the blood vessel; advancing a dilator and a sheath over the guidewire into the blood vessel; withdrawing the guidewire and the dilator while maintaining a position of the sheath within the blood vessel; and/or before puncturing the blood vessel with the needle, further including one or more of the following: advancing the guidewire through a guidewire port of a luer; the luer is connected to the needle to position the needle as desired relative to the blood vessel; the guidewire port is angled relative to a longitudinal axis of the needle, the guidewire port positioning the proximal portion of the guidewire at a predetermined angle relative to the longitudinal axis of the needle; inserting the needle into an opening in the guidewire, the opening positioned on a middle portion of guidewire, the middle portion between the proximal portion and the over-the-needle portion of the guidewire, the opening in communication with the lumen of the guidewire; advancing the needle adjacent the support wire into the lumen of the over-the-needle portion of the guidewire; and/or while the over-the-needle portion of the guidewire is being advanced into the blood vessel, the proximal portion of the guidewire advances through the guidewire port and is maintained at the predetermined angle relative to the longitudinal axis of the needle.

The foregoing is a summary and contains simplifications, generalization, and omissions of detail. Those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of any subject matter described herein.

BRIEF DESCRIPTION OF THE DRAWINGS

The foregoing and other features of the present disclosure will become more fully apparent from the following description, taken in conjunction with the accompanying drawings. Understanding that these drawings depict only some embodiments in accordance with the disclosure and are, therefore, not to be considered limiting of its scope, the disclosure will be described with additional specificity and detail through use of the accompanying drawings.

FIG. 9A illustrates an enlarged side view of an example embodiment of a guidewire.

FIG. 9B illustrates an enlarged side of a cross-section of an example embodiment of a guidewire.

FIGS. 10A-C illustrate an example method of using a vascular access system as discussed herein.

DETAILED DESCRIPTION

Figure 1:
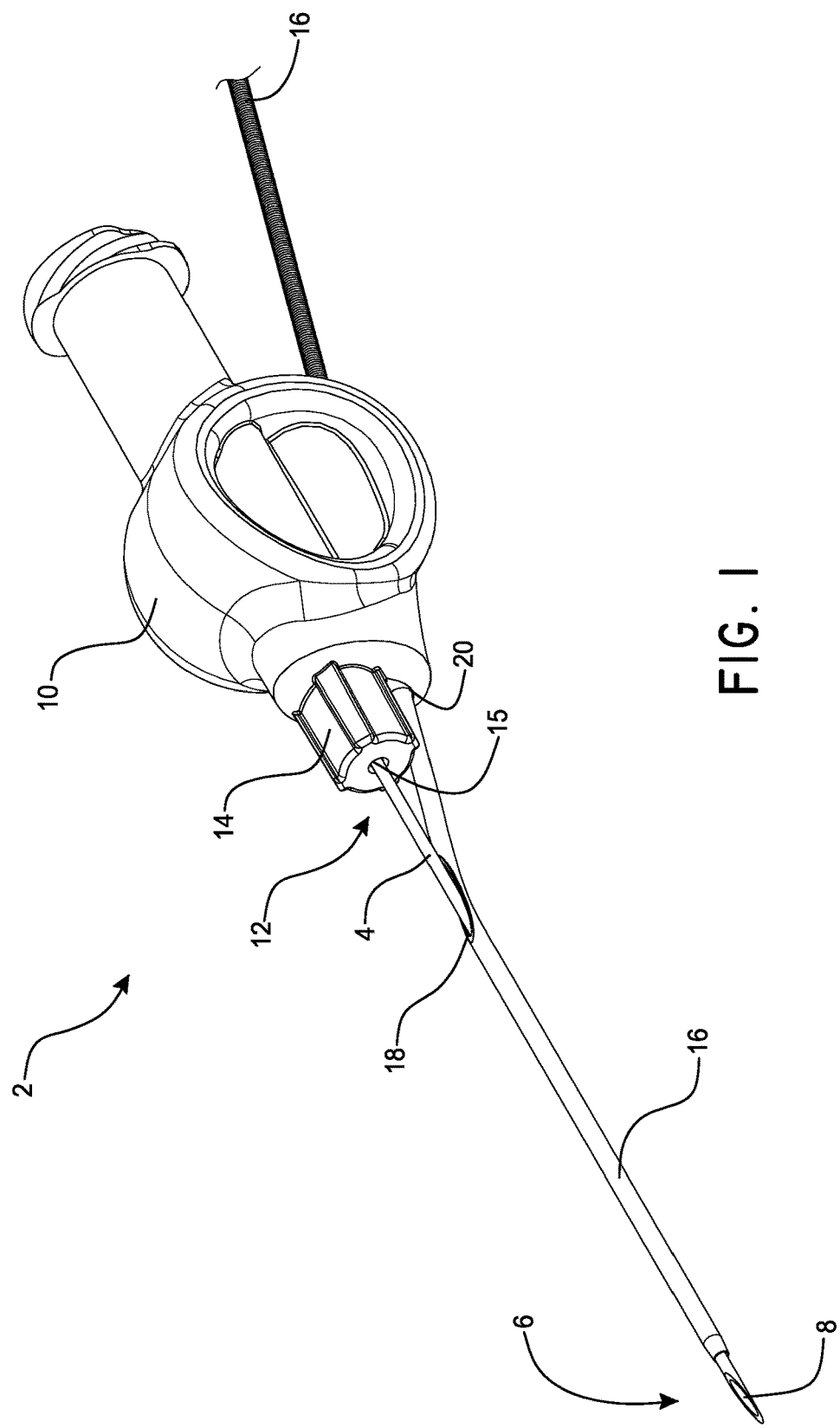
FIG. 1 illustrates a side, top, perspective view of an example embodiment of a vascular access system.

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments may be utilized, and other changes may be made, without departing from the spirit or scope of the subject matter presented here. It will be readily understood that the aspects of the present disclosure, as generally described herein, and illustrated in the figures, may be arranged, substituted, combined, and designed in a wide variety of different configurations, all of which are explicitly contemplated and made a part of this disclosure.

In particular, embodiments disclosed herein pertain to access devices or introducer sets used to obtain access (e.g., percutaneous) to a living body tissue (e.g., a body lumen, including canalization of blood vessels) to facilitate the passage of catheters through tissue and vascular walls while reducing the number of components threaded over a guidewire.

FIG. 1 illustrates a side, top, perspective view of an example embodiment of a vascular access system 2. The vascular access system 2 can have a needle 4 (e.g., a cannula). The needle 4 can have a sharpened distal end 6 (e.g., a beveled end) to allow for percutaneous access of body tissue. The needle 4 can have a central lumen 8.

The needle 4 can be, for example, a 24 gauge needle. In some embodiments, the needle 4 can have a 0.022" (inch) outer diameter (OD), 0.012 to 0.014" (inch) inner diameter, and a length of about 3.5" (inches). In some embodiments, the needle 4 can have any other appropriate gauge, including 19 gauge (0.042" OD, 0.027" ID), 20 gauge (0.036" OD, 0.023" ID), 21 gauge (0.032" OD, 0.020" ID), 22 gauge (0.028" OD, 0.016" ID), 22 s gauge (0.028" OD, 0.006" ID), 23 gauge (0.025" OD, 0.013" ID), gauge 25 (0.020" OD, 0.010" ID), 26 gauge (0.018" OD, 0.010" ID), 26 s gauge (0.018" OD, 0.006" ID), 27 gauge (0.016" OD, 0.008" ID), and 28 gauge (0.014" OD, 0.007" ID), including smaller or larger gauge needles and the corresponding outer and inner diameters, and any ranges involving any of the aforementioned dimensions, including from a 24 gauge to a 18 gauge needle, or from a 24 gauge to a 20 gauge needle for example, and overlapping ranges thereof. In some embodiments, the length of the needle 4 can appropriately correspond to a length of the third distal section of the guidewire 16 as discussed herein. The length of the needle 4 (e.g., an entire length) can be less than about 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, or 4.5 inches, and more than 4.5 inches, including the foregoing values and ranges bordering therein, such as between about 2.5 inches and about 4.5 inches, or between about 3 inches and about 4 inches for example. The needle 4 can be made of, for example, stainless steel, nitinol (nickel titanium), and/or other suitable metals or metal alloys. The composition of the needle 4 composition can provide echogenicity (e.g., the ability to bounce an echo, such as return a signal in ultrasound examinations).

The vascular access system 2 can have a luer 10. The needle 4 of the vascular access system 2 can have a proximate needle end 12. The proximate needle end 12 can be connected to the luer 10. The central lumen 8 of the needle 4 can be fluidly connected to an input port 36 of the luer 10 as discussed here in, and in particular, as discussed in reference to FIG. 4. The luer 10 can be made of, for example, a polymer. The luer 10 can polycarbonate. The luer 10 can be substantially clear or transparent to allow for viewing the guidewire lumen 20 and port 36. Having a viewable guidewire lumen 20 can facilitate observing whether the guidewire 16 is properly translating through the guidewire lumen 20 as discussed herein. Having a viewable port 36 can facilitate viewing bleedback or a flash during insertion the needle 4 into body tissue. In some embodiments, the luer 10 can be made of polymers including, for example, polyethylene terephthalate (PET), metalized PET, low-density polyethylene, high-density polyethylene, nylon, polyolefin, blends of polyolefin, polystyrene, blends of polyolefin and polystyrene, polyester, blends of polyester, etc.

The luer 10 can have a needle adapter 14. The needle 4 can be connected to the luer 10 via the needle adapter 14. The needle adapter 14 can be sized and shaped to correspond to and securely engage the needle 4 in position relative to the luer 10. The needle adapter 14 can have an adapter port 15 that engages, mates, and/or connects to the needle 4 to secure the needle relative to the luer 10. The needle adapter 14 can be made from the same or different materials as the luer 10 as discussed herein. The needle adapter 14 can be substantially clear or transparent as discussed herein for the luer 10.

The vascular access system 2 can have a guidewire 16. The guidewire 16 can have a skive 18 (e.g., an opening, aperture, or slot formed in the guidewire 16) that provides an opening for a passageway through the guidewire 16 as discussed herein (e.g., the skive 18 communicates with and provides access to a lumen of the guidewire 16). The needle 4 for can be inserted into the skive 18 and the guidewire 16 to slide over the needle 4. The guidewire 16 can be sized and shaped to correspond to the outer diameter of the needle 4. For example, the inner diameter of the guidewire 16 can correspond to or be about the same size as the outer diameter of the needle 4 as discussed herein. The inner diameter of the guidewire 16 can be sized to provide a secure fit over the needle 4 without the guidewire 16 freely sliding off of the needle 4 (e.g., without the application of an external force). Concomitantly, the inner diameter of the guidewire 16 can be sized to provide sufficient clearance relative to the outer diameter of the needle 4 for the guidewire 16 to slide off the needle 4 when desired (e.g., when a user applies an external force to the guidewire 16 and pulls out the needle 4). The inner diameter of the guidewire 16 can be sized to accommodate the core wire 42 (e.g., the ribbon 44) while the needle 4 is in the guidewire 16 as discussed herein.

As illustrated in FIG. 1, the luer 10 can have a guidewire lumen 20. In some embodiments, the guidewire lumen 20 is not fluidly connected to the adapter port 15 and/or port 36 of the luer 10. The guidewire lumen 20 can be configured to slidably accept and/or engage the guidewire 16. The guidewire lumen 20 can be sized and shaped such that the guidewire 16 can slide (e.g., relatively freely slide or with minimal impedance), within the guidewire lumen 20 as discussed herein, and can also advantageously assist in guiding the guidewire 16 as it moves over the needle 4, and reduce the possibility of fraying or other damage to the guidewire 16, such as proximate the skive 18. The guidewire lumen 20 can be oriented within the luer 10 to direct, position, and/or hold the guidewire at a predetermined angle relative to the needle 4 and/or luer 10 as discussed herein, and in particular, as discussed in reference to FIGS. 2 and 4. In FIG. 1, the proximal guidewire 16 and associated guidewire lumen 20 is shown as generally inferior to the luer. However, in some embodiments, the proximal guidewire 16 and associated guidewire lumen 20 can be positioned generally superior to the luer 10, or laterally in other embodiments.

Figure 2:
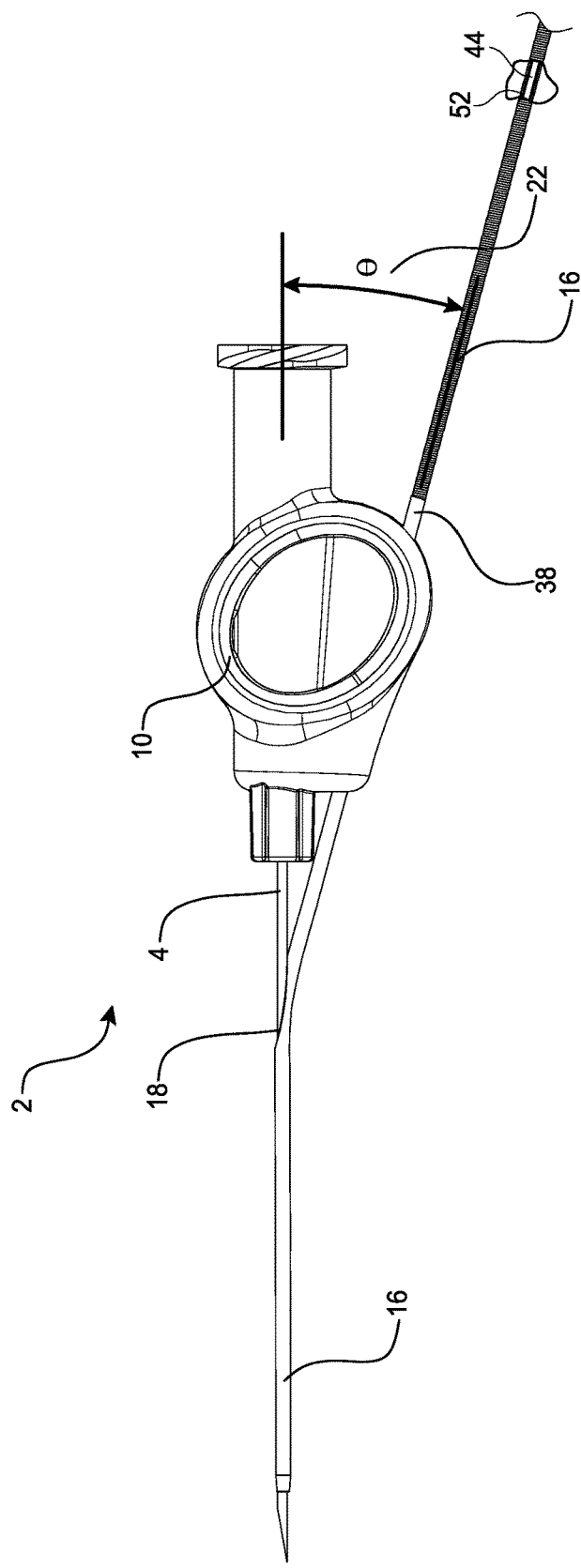
FIG. 2 illustrates a side view of an example embodiment of a vascular access system.

FIG. 2 illustrates a side view of an example embodiment of a vascular access system 2. As illustrated in FIG. 2, the guidewire 16 can pass through a central body of the luer 10. For example, the guidewire 16 can pass through the guidewire lumen 20 as discussed herein. The guidewire lumen 20 can direct and/or position the guidewire 16 at a predetermined guidewire angle θ 22. In some embodiments, the guidewire angle 22 can be about 15 degrees. In some embodiment, the guidewire angle 22 can range between about 5 to 45 degrees, including about 5 to 35, 5 to 30, 5 to 25, 5 to 20, 5 to 15, 5 to 10, 10 to 35, 10 to 30, 10 to 30, 10 to 25, 10 to 20, 10 to 15 degrees, including the foregoing values and ranges bordering therein. The guidewire angle 22 can be considered relative to the longitudinal axis of the needle 4 (e.g., central lumen 8 of the needle and/or a longitudinal axis of the port 36, see FIG. 4).

The guidewire angle 22 can be varied depending on the guidewire lumen 20 directing the pushability of the guidewire 16 (e.g., due to the core wire 42 as discussed herein) along the needle 4 as desired. Accordingly, the guidewire angle 22 can vary based on the design of the guidewire 16. As discussed herein, the guidewire 16 may vary in stiffness to enhance the pushability or ability of the vascular access system 2 to push the guidewire 16 through and into the living tissue (e.g., vasculature). The stiffer the guidewire 16, the smaller guidewire angle 22 may be, in some cases. A balance may be achieved between a stiffness and/or rigidity of the guidewire 16 and the guidewire angle 22 imparted on the guidewire 16 by the luer 10 for a desired pushability or ability of the vascular access system 2 to push the guidewire 16 through and into the living tissue (e.g., vasculature). The guidewire angle 22 may also vary depending the comfort or ability to push the guidewire 16 along the needle 4.

In some embodiment, the stiffness and/or rigidity of the guidewire 16 and/or the guide angle 22 may vary depending on procedure to be performed. For example, if the body tissue to be accessed is an awkward or difficult position to reach, a varying stiffness guidewire 16 and/or guidewire angle 22 may be chosen for the desired procedure. As another example, if the body tissue is "thick" at a desired location, corresponding stiffness guidewire 16 and/or guidewire angle 22 may be chosen. Varying stiffness of guidewires 16 and/or luers 10 with varying guidewire angles 22 may be provided in a kit and chosen by a user depending on desired pushability and/or body tissue site as discussed herein. In some embodiments, the guidewire 16 has a first stiffness proximally and a second stiffness distally, the first stiffness being greater than the second stiffness. In some embodiments, the guidewire has a Shore durometer in a proximal portion that is about or at least about 10%, 20%, 30%, 40%, 50%, 75%, 100%, 150%, 200%, or more greater than a durometer in a distal portion of the guidewire.

Figure 3:
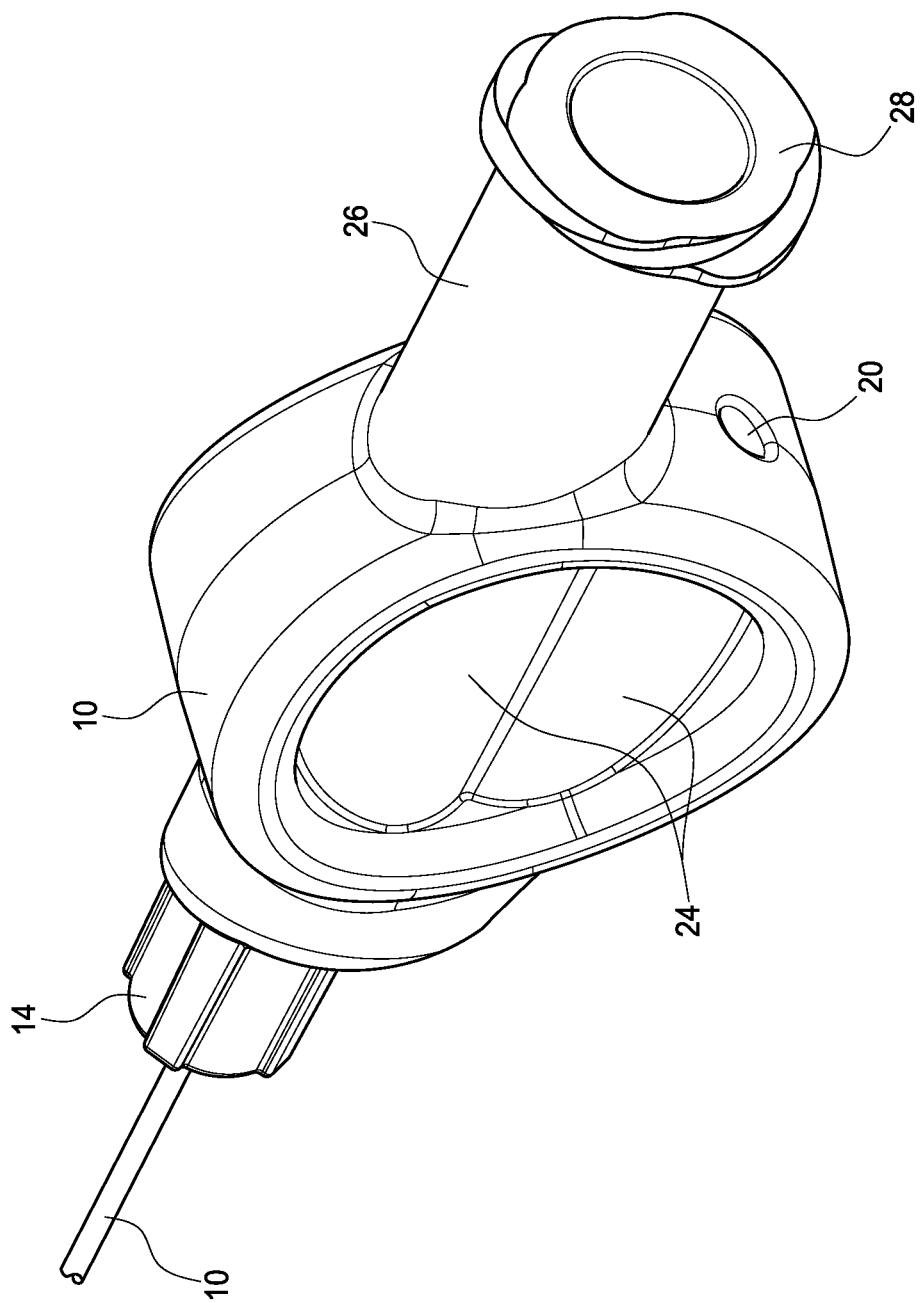
FIG. 3 illustrates a side, top, perspective view of an example embodiment of a luer.

FIG. 3 illustrates a side, top, perspective view of an example embodiment of a luer 10. The luer 10 can have a hub 26. The hub 26 can be shaped and sized to engage, mate with, and/or connect to any standard adapter of, for example, a syringe. The hub 26 can mate with other suitable medical device. The hub 26 can have a lock fitting 28. The lock fitting 28 can securely engage a hub of a syringe or securely engage any other suitable medical device. The lock fitting 28 can be threaded to mate with other threaded connections. The hub 26 and/or lock fitting 28 can be made from the same or different materials as the luer 10 as discussed herein. The hub 26 and/or lock fitting 28 can be substantially clear or transparent as discussed herein for the luer 10.

The luer 10 can have gripping panels 24. The gripping panels 24 can be sized and shaped to facilitate a user holding (e.g., gripping with fingers) and guiding the vascular access system 2 for percutaneous access of body tissue as discussed herein. As illustrated, the gripping panel 24 can include rounded panels on the luer 10 that provide channels and/or grooves for a user to comfortably grip the luer 10.

Figure 4:
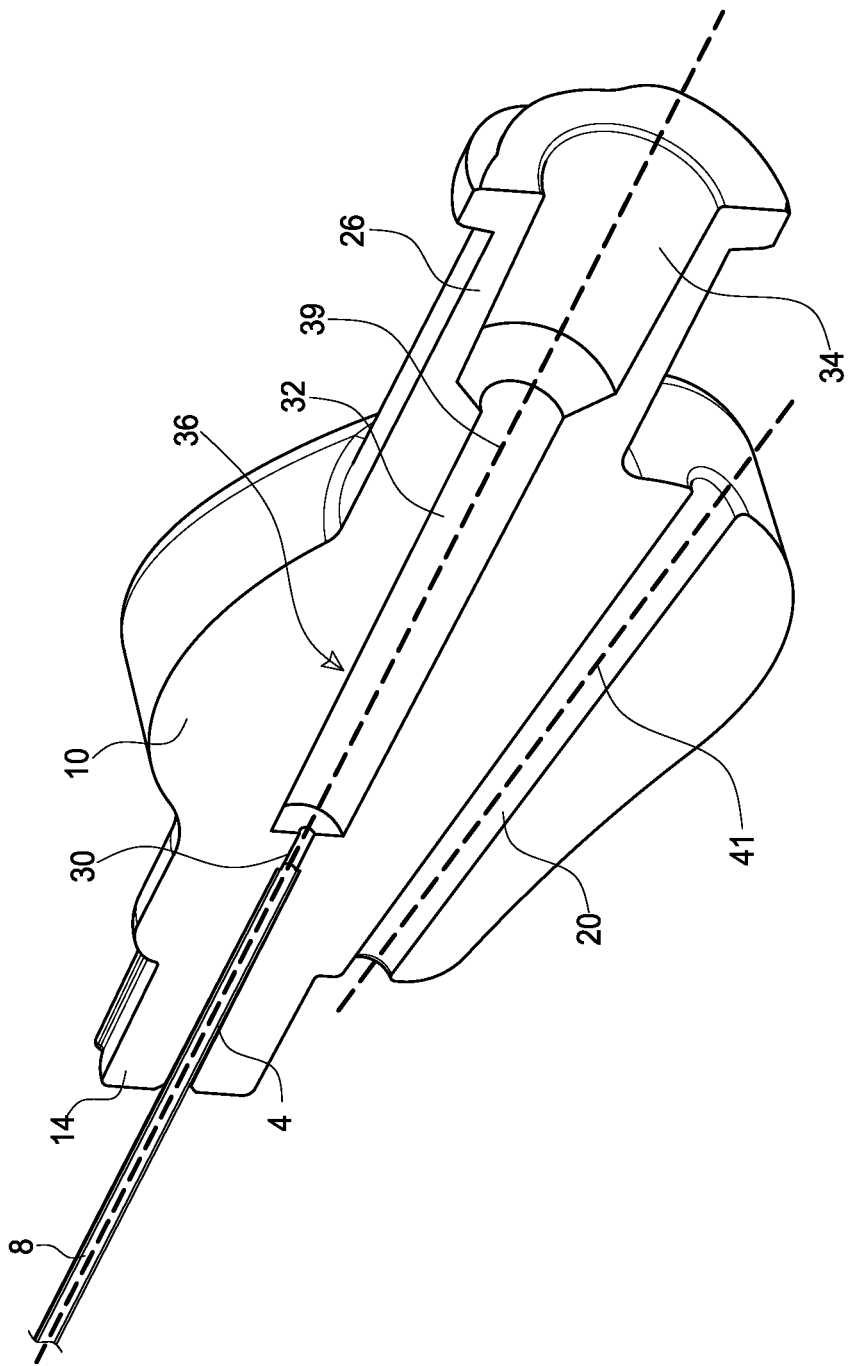
FIG. 4 illustrates a side, top, perspective view of a cross-section of an example embodiment of a luer.

FIG. 4 illustrates a side, top, perspective view of a cross-section of an example embodiment of a luer 10. As discussed herein, the needle adapter 14 can be sized and shaped to correspond to and engage, mate with, and/or connect to the needle 4 in position relative to the luer 12. The needle adapter 14 can have an adapter lumen 30 that securely engages the needle 4. A section of the adapter lumen 30 (e.g., proximal section) can have an inner diameter that corresponds to an inner diameter of a central lumen 8 of the needle 4. A section of the adapter lumen 30 (e.g., distal section) have an inner diameter that corresponds to an outer diameter of the needle 4. The inner diameter of, for example, the distal section of the adapter lumen 30 can be sized and shaped to securely engage the needle 4 as discussed herein.

The luer 10 can have a luer lumen 32. The luer lumen 32 can be fluidly connected to the adapter lumen 30. The luer lumen 32 can fluidly connect to a hub lumen 34. The hub lumen 34 can be sized and shaped to correspond to and engage, mate with, and/or connect to a medical device such as, for example, a syringe. An adapter of a syringe can be inserted into the hub lumen 34. The diameter of the luer lumen 32 can correspond to an inner diameter of, for example, a syringe adapter to facilitate fluid flow between the needle 4, luer 10, and/or for example, a syringe. The combination of or anyone of the adapter lumen 30, luer lumen 32, and/or hub lumen 34 can be considered a port 36 of the luer 10 fluidly connecting a medical device (e.g., a syringe) connected to the luer 10 via the hub 26 to the needle 4 connected to the luer 10 via the adapter 14. The combination of or anyone of the adapter lumen 30, luer lumen 32, and/or hub lumen 34 can be axially aligned along a longitudinal axis 39 to form the port 36 of the luer 10.

As illustrated in FIG. 4, the guidewire lumen 20 and the port 36 can be independent of each other and the luer 10. Stated differently, the guidewire lumen 20, in some embodiments, is not in fluid communication with the port 36 of the luer 10 and/or the central lumen 8 of the needle 4. The guidewire lumen 20 can extend along a longitudinal axis 41 (e.g., along a straight line). The configuration of the guidewire lumen 20 not being in fluid communication with the port 32 can allow for the desired positioning of the guidewire 16 (e.g. providing a desired/predetermined guidewire angle 22) while still allowing for the functionality of the vascular access system 2 to provide indication of bleedback or flash during insertion of the needle 4 and guidewire 16 in body tissue as discussed herein.

As illustrated in FIG. 4, the guidewire lumen 20 can be substantially straight through a body of the luer 10 (e.g., along the longitudinal axis 41). The guidewire loom and 20 can be straight to provide a smooth travel path to the guidewire 16 as discussed herein. For example, the guidewire 16 can smoothly transition or slide within the guidewire lumen 20 with minimal impedance or obstruction. The axial orientation of the guidewire lumen 20 relative to the axial orientation of the port 36 (e.g., orientation of the longitudinal axis 39 and the longitudinal axis 41) can impart the guidewire angle 22 on the guidewire 16 when the guidewire 16 is disposed over the needle 4 as discussed herein. For example, a substantially straight guidewire lumen 20 can be oriented at the angle guidewire 22 relative to the port 36 that is axially aligned with the needle 4 to impart the guidewire angle 22 to the guidewire 16 at the skive 18 relative central lumen 8 of the needle 4 and/or a central axis of the guidewire over the needle 4. In reference to FIG. 4, the central axis of the guidewire 16 can coincide with the central axis of the guidewire 16 portion over the needle 4.

Figure 5:
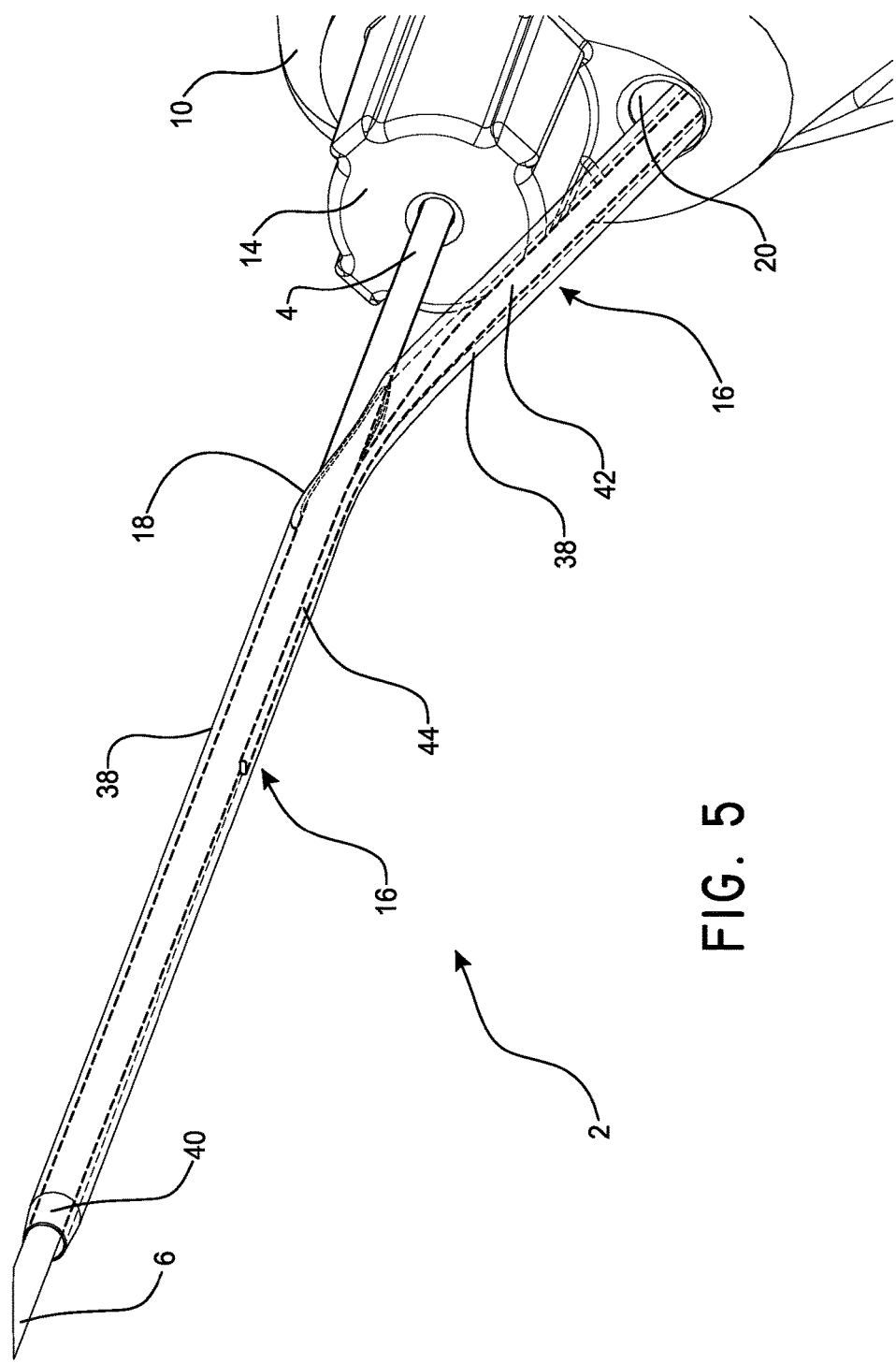
FIG. 5 illustrates a side, bottom, perspective view of an example embodiment of a vascular access system.

FIG. 5 illustrates a side, bottom, perspective view of an example embodiment of a vascular access system 2. A portion of the guidewire 16 is shown transparently for illustration purposes. In particular, a tip (e.g., tube) 38 of the guidewire 16 is shown transparently to illustrate other components of the guidewire 16 as discussed herein. The tip 38 of the guidewire 16 can have an inner diameter (e.g., lumen of the tip 38/guidewire 16) that corresponds to an outer diameter of the needle 4 as discussed herein. The inner diameter can be shaped to accommodate the outer diameter of the needle 4 as discussed herein to provide a secure fit (e.g., not slide freely slide off the needle 4), but provide clearance sufficient to slide the tip 38 from the needle 4 when desired. For example, the tip 38 can correspond to a 21 gauge ID and OD when a needle 4 corresponds to 24 gauge ID and OD. In an example embodiment, the needle 4 can have about a 0.022" OD while the tip 38 can have about a 0.024" ID. A relatively larger inner diameter of the guidewire 16 relative to the outer diameter of the needle 4 can be sized to accommodate the ribbon 44 as discussed herein.

A distal section 40 of the tip 38 can be tapered. The distal section 40 of the tip 38 can taper at or near the distal end 6 of the needle 4 to substantially the OD of the needle 4. The tapered distal section 40 can provide smooth stretching (rather than tearing) of the body tissue as the needle 4 is advanced through the body tissue (e.g., an atraumatic tip).

In some embodiments, the tip 38 of the guidewire 16 can be made of polymer such as integrally thermoformed plastic. In some embodiments, the tip 38 can be made from polymers such as fluorinated ethylene propylene (FEP) and/or polytetrafluoroethylene (PTFE). In some embodiments, the tip 38 can be made of polymers such as polyethylene terephthalate (PET), metalized PET, low-density polyethylene, high-density polyethylene, nylon, polyolefin, blends of polyolefin, polystyrene, blends of polyolefin and polystyrene, polyester, blends of polyester, etc. The tip 38 of the guidewire 16 can be made of any suitable material, including the aforementioned material, to provide a flexible tip 38 of the guidewire 16 that is able to engage (slide over) needle 4 and bend to a desired guidewire angle 22 as discussed herein. The tip 38 can include radiopaque fillers that can increase the opacity of guidewire 16 to, for example, make the guidewire 16 visible under fluoroscopy and/or x-rays without or minimally sacrificing the mechanical properties of the polymer(s) of the guidewire 16 as discussed herein. The composition of the tip 38 can provide echogenicity (e.g., the ability to bounce an echo, such as return a signal in ultrasound examinations). The composition and features of the tip 38 as discussed herein can provide a guidewire 16 that is atraumatic (e.g., causing minimal tissue injury upon insertion into body tissue).

The guidewire 16 can have a core wire (e.g., support wire or pushing wire) 42 that runs concentric with the guidewire 16 through a portion of the tip 38. The core wire 42 can be sized and shaped to fit within the tip 38 of the guidewire 16. For example, in certain sections of the guidewire 16, the core wire 42 can have an outer diameter that corresponds to the inner diameter of the tip 38 of the guidewire 16. The outer diameter of the core wire 42 can be a similar diameter as the outer diameter of the needle 4. In some embodiments, the outer diameter of the core wire 42 may relatively larger than the outer diameter of the needle 4 such that the core wire 42 securely engages the guidewire 16, tip 38, and/or other sections of the guidewire 16. For example, the outer diameter of the tip 38 can be sized to prevent or inhibit movement of the core wire 42 within the tip 38 and/or other section of the guidewire 16. As illustrated in FIG. 5, an assembly of the tip 38 and core wire 42 can extend into the guidewire lumen 20 to pass through the luer 10 as discussed herein.

The core wire 42 can be made of any suitable rigid or stiff material to achieve pushability of the guidewire 16 as discussed herein. In some embodiments, the material of the core wire 42 can be stainless steel, nitinol (nickel titanium), and/or other suitable metals or metal alloys. In some embodiments, the core wire 42 can be of any suitable rigid or stiff polymer as discussed herein for the tip 38, but with increased rigidity or stiffness relative to the tip 38 that can be achieved via either the process in forming the core wire 42 and/or types or blends of materials used.

As illustrated in FIG. 5, the core wire 42 can gradually reduce in diameter and/or size in the guidewire 16 leading to the skive 18. The core wire 42 can gradually and/or smoothly taper from the outer diameter of the core wire 42 as discussed herein to a ribbon 44. The tapering of the core wire 42 can begin, for example, at or near the guidewire lumen 20 in the luer 10. As illustrated in FIG. 5, the tapering of the core wire 42 can begin more proximate to the needle 4 relative to the guidewire lumen 20. For example, in an embodiment, proximal to the guidewire lumen 20, the core wire 42 can be about 0.015" in diameter (e.g., outer diameter). As the core wire 42 approaches the skive 18, the core wire 42 can taper to about 0.010" in diameter (e.g., while still remaining substantially circular or round). In some embodiments, the core wire 42 can taper from a first larger diameter to a second smaller diameter that is about, no more than about, or at least about 10%, 15%, 20%, 25%, 30%, 35%, 40%, 45%, 50% less than the first diameter, or between about 25% and about 40% less than the first diameter.

Figure 6:
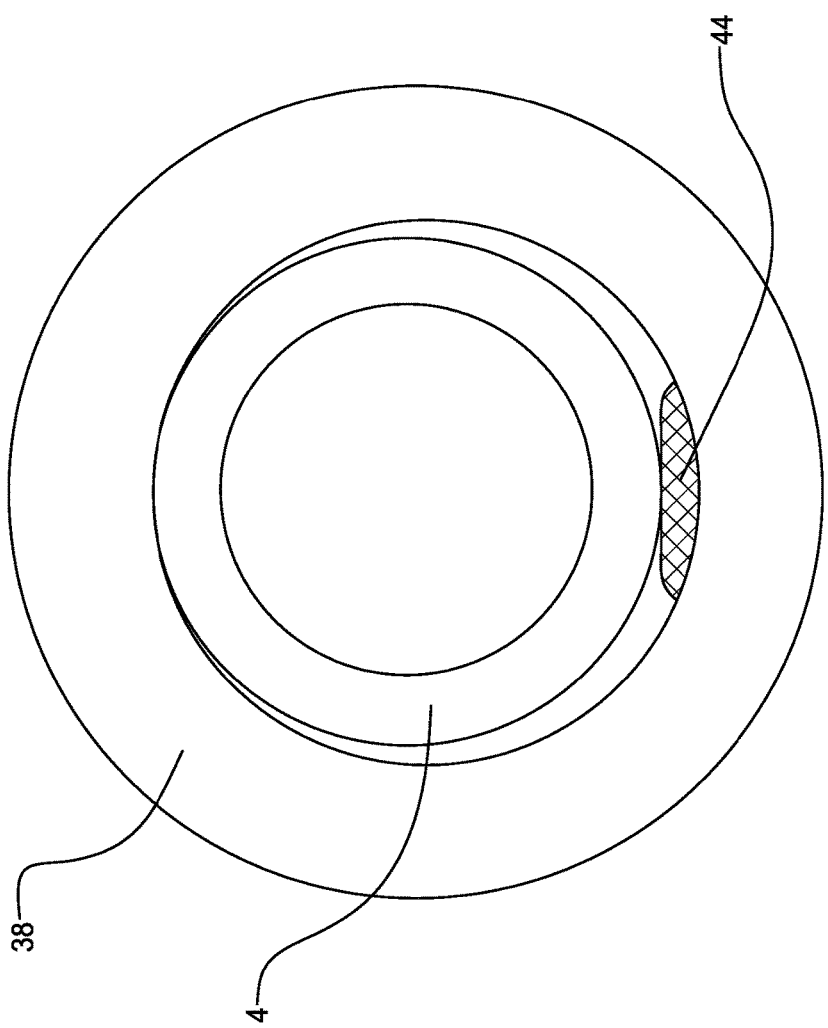
FIG. 6 is a cross-sectional profile view of an example embodiment of a tip, a needle, and a ribbon.

As the core wire 42 extends near the skive 18 and past the skive 18, the core wire 42 can taper down to the ribbon 44, which can be about 0.004"×0.010" at the distal end of the ribbon 44 (e.g., approaching the distal end 6 of the needle 4). In reference to the orientation of the ribbon 44 as illustrated in FIG. 6, the ribbon can be about 0.004" in height and about 0.010" in width. In some embodiment, a first dimension or the height (in reference to FIG. 6) of the ribbon 44 may be about 0.001, 0.002, 0.003, 0.004, 0.005, 0.006, 0.007, 0.008, 0.009, or 0.010", including the foregoing values and ranges bordering therein, such as between about 0.001" and about 0.010", or between about 0.002" and about 0.006" for example. In some embodiment, a second dimension or the width (in reference to FIG. 6) of the ribbon 44 may be about 0.005, 0.006, 0.007, 0.008, 0.009, 0.010, 0.011, 0.012, 0.013, 0.014, 0.015, 0.016, 0.017, 0.018, 0.019 and 0.020", including the foregoing values and ranges bordering therein, such as between about 0.005" and about 0.020", or between about 0.007" and about 0.015" for example. The dimensions discussed herein in reference to the core wire 42 and/or ribbon 44 can vary to correspond to the possible variation in dimensions of the needle 4, gauge wire 16, tip 38, and/or coil wire 52 (see FIG. 8) as discussed herein, and in particular as discussed herein in reference to the variation in dimension of the diameters of the needle 4.

The core wire 42 can taper to a ribbon 44 that can at least partially occlude the skive 18. In some embodiments, the core wire 42 and/or ribbon 16 can occlude a majority or all of the skive 18. In some embodiments, when the needle 4 is pushed into and through the skive 18 along the tip 38, the needle 4 pushes against the core wire 42 and/or ribbon 44 such that the material of the tip 38 is stretched or fits closely over the needle 4 and core wire 42 and/or ribbon 44 to create a secure engagement between the needle 4 and guidewire 16 as discussed herein.

The ribbon 44 can taper in size or continue to gradually and/or smoothly taper in size from the skive 18 along a length of the needle 4 (e.g., along a direction to the distal end 6 of the needle 4). As illustrated in FIG. 5, the ribbon 44 can run or extend adjacent to the needle 4, proceeding distally to the skive 18. The ribbon 44 can terminate proximate to a midpoint of the needle 4. In some embodiments, the ribbon 44 may terminate proximate to the skive 18. In some embodiments, the ribbon 44 may terminate proximate to the distal section 40 of the tip 38. The ribbon 44 can terminate anywhere along a length of the engagement of the tip 38 over the needle 4.

As illustrated in FIG. 5, the core wire 42 can be substantially round with a diameter corresponding to the inner diameter of the tip 38. As the core wire 42 tapers and/or transitions to the ribbon 44 as discussed herein, the profile of the core wire 42 can reduce and/or flatten to a profile as illustrated in FIG. 6 (e.g., rectangular).

FIG. 6 is a cross-sectional profile view of an embodiment of a tip 38, a needle 4, and a ribbon 44. As illustrated in FIG. 6, the tip 38 surrounds, contains, houses, and/or envelops the needle 4 and the ribbon 44. The inner diameter of the tip 38 corresponds to the outer diameter of the needle 4 and the ribbon 44 such that the ribbon 44 rests against or is pressed against the corresponding surfaces of the tip 38 and the needle 4. In some embodiments, the ribbon 44 can be imbedded into the material of the tip 38. As illustrated in FIG. 6, the tip 38 can have a predetermined internal diameter that can accommodate both the needle 4 and the ribbon 44 without or substantially sacrificing the structural integrity of the tip 38 (e.g., tearing the polymer of the tip 38). As illustrated in FIGS. 5 and 6, the tapering core wire 42 and/or ribbon 44 can run opposite to the skive 18 and/or along the needle 4 for reinforcement of the adjacent/mating components and to allow for pushability forces to be transferred adequately when the user pushes the guidewire 16 over the needle 4 and into the body tissue (e.g., vasculature)

As discussed herein, a balance may be achieved between a stiffness and/or rigidity of the guidewire 16 and the guidewire angle 22 imparted on the guidewire 16 by the luer 10 for a desired pushability or ability of the vascular access system 2 to push the guidewire 16 through and into the living tissue (e.g., vasculature). Further, the extension of the core wire 42 through the guidewire 16 and tapering into the ribbon 44 to run adjacent the needle 4 as discussed herein can achieve desired pushability of the guidewire 16 by, for example, the guidewire 42 (and ribbon 44) transferring the pushability forces along the needle 4 (e.g., shaft of the needle 4) to allow the guidewire 16 to pass through the body tissue (e.g., skin) into, for example, the vasculature. Stated differently, the core wire 42 and the ribbon 44 provide for the pushability of the guidewire 16 (e.g., ability to push through and enter body tissue when a user pushes on the guidewire 16, such as at the coil 52).

Figure 7:
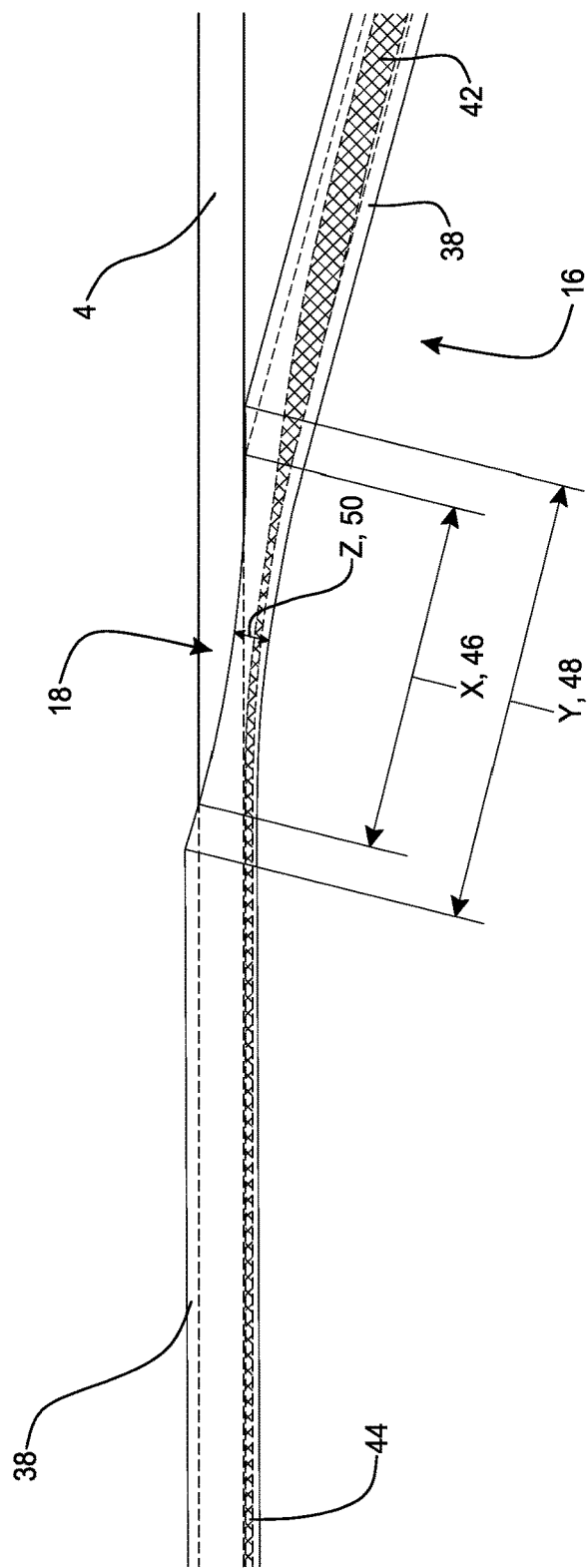
FIG. 7 illustrates a side view of an example embodiment of a needle and a guidewire over the needle.

FIG. 7 illustrates a side view of an example embodiment of a needle 4 and a guidewire 16 over the needle 4. The guidewire 16 is shown transparently for illustration purposes. In particular, the tip 38 of the guidewire 16 is shown transparently to illustrate other components of the guidewire 16 as discussed herein. The guidewire 16 can have a skive 18 as discussed herein that can be in communication with or open to a lumen of the guidewire, and in particular, in communication with or open to a lumen formed by a tip 38. As discussed herein, the core wire 42 in the tip 38 can correspond substantially to an inner diameter of the tip 38 at certain portions of the guidewire 16. As the core wire 42 approaches the skive 18, the core wire 42 tapers to at least partially occlude the opening of the skive 18. The core wire 42 tapers into the ribbon 44 that can extend adjacent the needle 4 in the tip 38 such that pushability forces on guidewire 16 are communicated through the core wire 42 along the needle 4 as discussed herein.

The skive 18 can have a skive opening 46 with a dimension X. In an embodiment, the skive opening 46 can be about 0.060" in length X corresponding to, for example, the tip 38 has a 0.024" ID and 0.035" OD as discussed herein. In some embodiments, the skive opening 46 can have a length X of about 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, and 0.070", including the foregoing values and ranges bordering therein, between about 0.030" and about 0.100", between about 0.050" and about 0.070", or between about 0.055" and about 0.065" for example.

The skive 18 can have a skive length 48 with a dimension Y. In an embodiment, the skive length 48 can be about 0.080" in length Y when, for example, the tip 38 has a 0.024" ID and 0.035" OD as discussed herein. In some embodiments, the skive opening 46 can have a length Y of about 0.070, 0.071, 0.072, 0.073. 0.074, 0.075, 0.076, 0.077, 0.078, 0.079, 0.080, 0.081, 0.082, 0.083, 0.084, 0.085, 0.086, 0.087, 0.088, 0.089, and 0.090", including the foregoing values and ranges bordering therein, between about 0.050" and about 0.100", between about 0.070" and about 0.090", or between about 0.075" and about 0.085" for example.

The skive 18, skive opening 46, and/or skive length 48 can be sized and shaped to achieve a predetermined skive support 50. The skive support 50 can be a minimum material length Z of the tip 38 material that is retained in the tip 38 after the skive 18 is fabricated (e.g., cut out of the tip 38, or any other suitable manufacturing method). As illustrated in FIG. 7, the skive support 50 can be a minimum length Z of material between a point on the skive 18 and the tip 38. In some embodiments, the skive support 50 length Z is a minimum predetermined length relative to the diameter of the tip 38. For example, the skive support 50 length Z can be a minimum length such that a perimeter or periphery of the skive 18 is above or does not cross a central axis of the tip 38 and/or guidewire 16 relative to the view illustrated side view of FIG. 7 (e.g., a plane along a central axis of the tip 38 extending perpendicularly from the view of FIG. 7). In such embodiments, a minimum amount of material of the tip 38 is present about or proximate to the skive 18 to support and retain the core wire 42, ribbon 44, and/or needle 4 in desired position and facilitate the transfer pushability of forces as discussed herein.

In an embodiment, skive support 50 can be about 0.025" in length Z when, for example, the tip 38 has a 0.024" ID and 0.035" OD as discussed herein. In some embodiments, the skive opening 46 can have a length Z of about 0.015, 0.016, 0.017, 0.018. 0.019, 0.020, 0.021, 0.022, 0.023, 0.024, 0.025, 0.026, 0.027, 0.028, 0.029, 0.030, 0.031, 0.032, 0.033, 0.034, and 0.035", including the foregoing values and ranges bordering therein, between about 0.010" and about 0.050", between about 0.015" and about 0.035", or between about 0.020" and about 0.030" for example, or any other suitable length to be greater than the central axis of the tip 38 as discussed herein.

Figure 8:
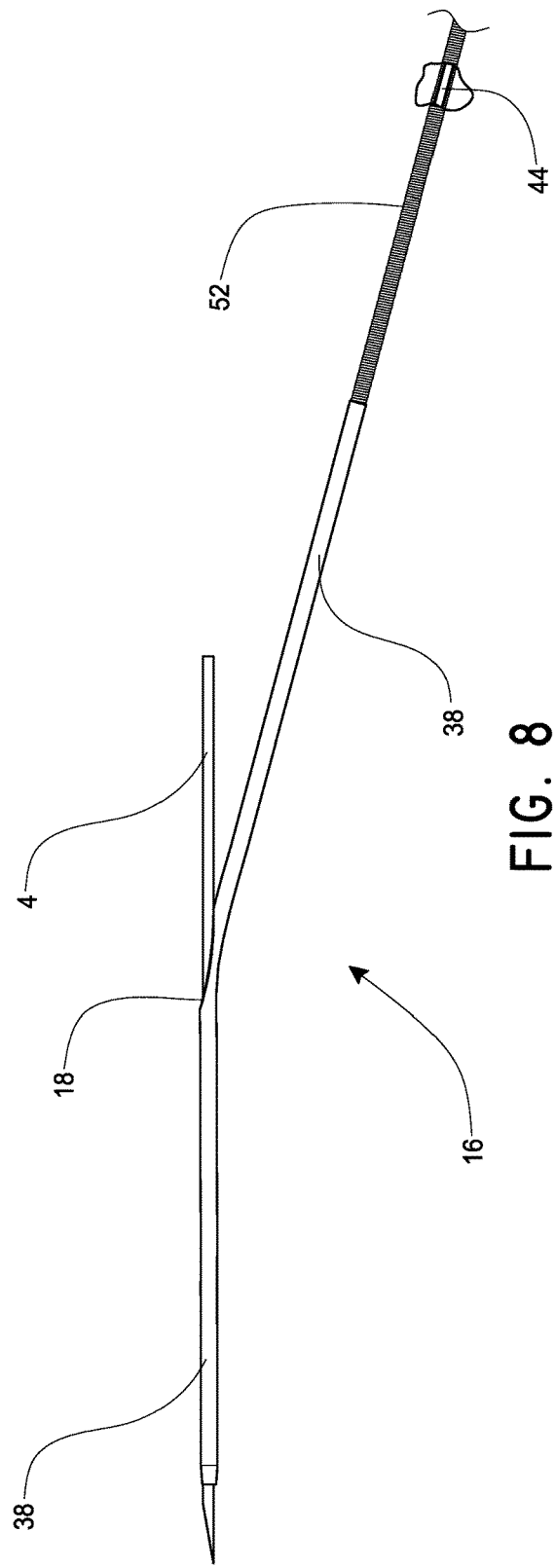
FIG. 8 illustrates a side view of an example embodiment of a guidewire.

FIG. 8 illustrates a side view of an embodiment of a guidewire 16. As discussed herein, the guidewire 16 can have a tip 38 with a skive 18. A needle 4 can enter the tip 38 via the skive 18. The guidewire 16 can have a coil 52 that connects to the tip 38 to form the guidewire 16.

FIG. 9A illustrates an enlarged side view of an embodiment of a guidewire 16. FIG. 9B illustrates an enlarged side of a cross-section of an embodiment of a guidewire 16. As illustrated in FIG. 9B, the coil 52 can be formed from coiled or winding material (e.g., wire, cord, cable, etc.) to form an inner diameter. The core wire 42 can continue through the coil 52 within the inner diameter of the coil 52 through the rest of the length of the guidewire 16 (e.g., proximal section of the guidewire 16 as discussed herein). The core wire 42 can be concentric to the coil 52. In some embodiments, the coil 52 of the guidewire 16 may be formed from a solid wire material without a central lumen for the core wire 42. For example, the core wire 42 may terminate at and/or be connected to the coil 52 (e.g., solid body wire). In some embodiments, the core wire 42 diameter may expand into the outer diameter of the guidewire 16 where the tip 38 terminates to form the third proximal section of the guidewire 16 as discussed herein.

The coiled or winding material of the coil 52 can be stainless steel, nitinol (nickel titanium), and/or other suitable metals or metal alloys. In some embodiments, the coil 52 can be made from or in addition with polymers as discussed herein, for example, in reference to the materials of the tip 38.

The coiled material of the coil 52 can be formed from, for example, a wire/cord/cable that has a diameter of 0.006" inches. In some embodiments, the diameter of the coiled or winding material that forms the coil 52 can be about 0.001, 0.002, 0.003, 0.004, 0.005, 0.006, 0.007, 0.008, 0.009, 0.010, 0.011, and 0.012", including the foregoing values and ranges bordering, including the foregoing values and ranges bordering therein, or any other suitable diameter to form the coil 52 as discussed herein, such as between about 0.001" and about 0.020", between about 0.002" and about 0.010", or between about 0.002" and about 0.008" for example. As illustrated in FIGS. 9A and 9B, the inner and out diameters of the coil 52 as formed by the coiled material can correspond to the inner and outer diameters of the tip 38. The inner and outer diameters can be diameters as discussed herein in reference to the tip 38 and/or guidewire 16. For example, in one embodiment, the outer diameter of the coil 52 is about 0.035" and the inner diameter is about 0.024".

Returning to FIG. 8, a section of the guidewire 16 having the coil 52 can be considered a first or proximal (relative to a user) section of the guidewire 16. As discussed herein, the first proximal section of the guidewire 16 can include the core wire 42 and the coil 52. A section of the guidewire 16 having the skive 18 can be considered a second or middle (relative to a user) section of the guidewire 16. As discussed herein, the second middle section of the guidewire 16 can include the tip 38, the core wire 42, the ribbon 44, and/or the skive 18. A section of the guidewire 16 with the tip 38 over or configured to be over the needle 4 can be considered a third or distal (relative to a user) section of the guidewire 16. As discussed herein, the third distal section can include the tip 38, the core wire 42, and/or the ribbon 44. Particular sections of the guidewire 16 may vary and the components that the particular sections include as part of the guidewire 16 may vary. Sections of the guidewire 16 as discussed herein are for discussion purposes and not limiting.

In some embodiments, the guidewire 16 can be about 18" in overall or entire length (e.g., the length of the combined lengths of the first, second, and third sections of the guidewire 16 as discussed herein). In some embodiments, the guidewire 16 can be about 12, 13, 14, 15, 16, 17, 19, 20, 21, 22, 23, 24, 25, 26, 27, 28, 29, or 30" in length, including the foregoing values and ranges bordering there, or any other suitable length of guidewire 16 to enter the body tissue and reach a desired location (e.g., lumen) or insertion length of the guidewire 16 into the body tissue, between about 6" and about 36", between about 12" and about 30", or between about 18" and about 26" for example. In some embodiments, the first proximal section of the guidewire 16 can have a length that is less than about 90, 85, 80, 75, 70, 65, 60, 55, 50, 45, 40, 35, 30%, or less with respect to the entire length of the guidewire 16, or between about 50-90%, about 60-85%, or about 60-80% of the entire length of the guidewire 16). In some embodiments, the first and second sections of the guidewire 16 can have a length that is less than about 70, 65, 60, 55, 50, 45, 40, 35, 30, 25, 20, 15, 10%, or less with respect to the entire length of the guidewire 16, or between about 20-60%, about 25-50%, or about 25-40% of the entire length of the guidewire 16. The second section of the guidewire 16 can be a length such that upon insertion of the tip 38 onto the needle 4, the second section (e.g., the tip 38) extends through an entire length of the guidewire lumen 20. In some embodiments, the guidewire 16 may not have sections as discussed herein and can have a solid core (no central lumen, and thus the first and second sections of the guidewire may not be an over-the-needle assembly).

Figure 10C:
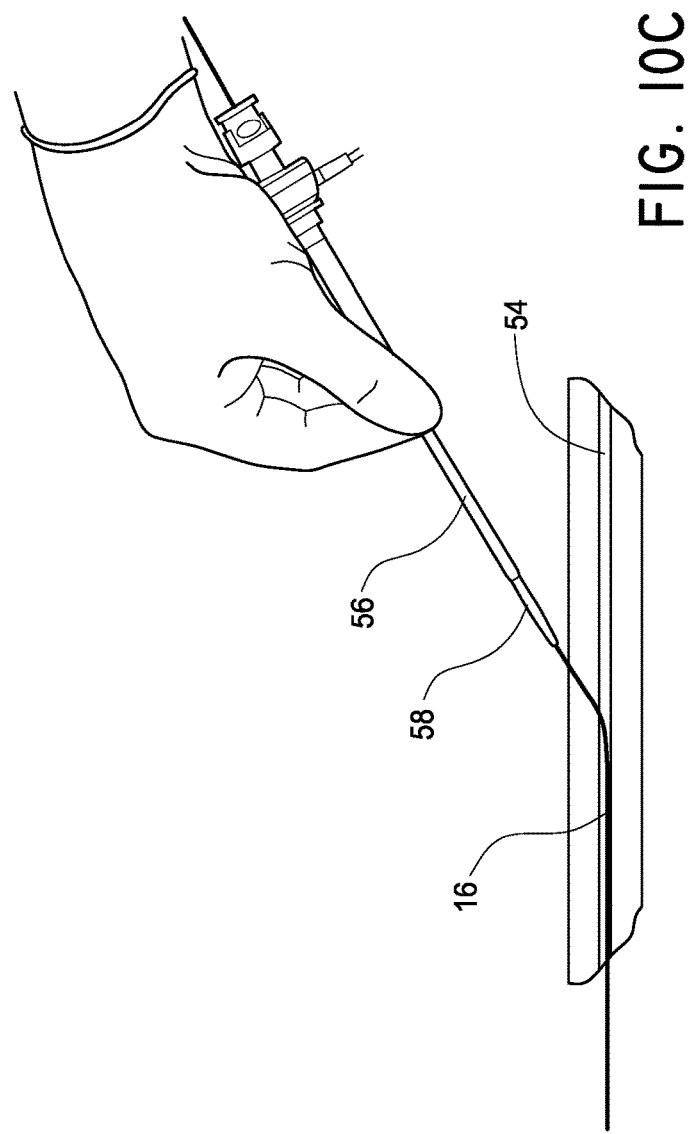

FIGS. 10A-D illustrate an example method of using the vascular access system 2 as discussed herein. FIGS. 10A-D illustrate accessing a body lumen 54, such as a blood vessel (e.g., body tissue as discussed herein), with the vascular access system 2. FIG. 10A illustrates puncturing the body lumen 54 with the vascular access system 2 (e.g., a needle loaded with an over-the-needle wire as discussed herein). Stated differently, the vascular access system 2, and particularly, the needle 4 and guide 16 are advanced into the body lumen 54. Upon accessing the body lumen 54, a user may see a backbleed or flash of blood in the luer 10 indicating access of the body lumen 54. In some embodiments, the procedure involves minimal or no blood dripping onto the operative field. Next (step not shown), the guidewire 16 can then be advanced into the body lumen 54 while substantially maintaining the position of the needle 4 relative to the body lumen 54. FIG. 10B illustrates withdrawing the needle 4 while maintaining the guidewire 16 in position relative to the body lumen 54. FIG. 10C illustrates inserting or advancing a sheath 56 and dilator 58 into the body lumen 54 over the guidewire 16. The sheath 56 and dilator 58 can have inner diameters greater than that of the outer diameter of the guidewire 16. After inserting the sheath 56 and dilator 58, the guidewire 16 and dilator 56 can be withdrawn, leaving the sheath 56 inside the body lumen 54. In some embodiments, puncturing the body lumen 54 can be via a percutaneous or cut-down approach. In some embodiments, the method could include, e.g., needle, wire, sheath, and dilator features as discussed herein. Following successful access into the body lumen, e.g., the artery or vein, various additional diagnostic and therapeutic procedures can be readily performed. For example, arterial or venous blood can be collected for diagnostic sampling. In some embodiments, the access can be used for rapid infusion of, for example, intravenous fluids such as saline, one or more therapeutic agents, or blood or a component product, for example. In some embodiments, a catheter can be inserted into the access port for performance of a procedure, such as angiography for example, Swan-Ganz catheterization, or delivery of a medical device such as a stent or heart valve, for example. In some embodiments, once access is obtained, the vascular access system or components thereof can be exchanged over-the-wire for a larger gauge catheter system, such as a Quinton or Mahurkar catheter for dialysis access for example.

The dilator-sheath assembly 56, 58 as discussed herein and in reference to FIG. 10D can include an introducer sheath 56 (e.g., a 12 French sheath), and a dilator 58 that can be about 0.035" OD compatible, for example. The introducer sheath 56 can have a central lumen sized and configured to house the over-the-needle guidewire 16 therethrough.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting a catheter into the internal jugular vein" includes "instructing the insertion of a catheter into the internal jugular vein." It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediary components. The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced embodiment recitation is intended, such an intent will be explicitly recited in the embodiment, and in the absence of such recitation no such intent is present. For example, as an aid to understanding, the disclosure may contain usage of the introductory phrases "at least one" and "one or more" to introduce embodiment recitations. However, the use of such phrases should not be construed to imply that the introduction of an embodiment recitation by the indefinite articles "a" or "an" limits any particular embodiment containing such introduced embodiment recitation to embodiments containing only one such recitation, even when the same embodiment includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce embodiment recitations. In addition, even if a specific number of an introduced embodiment recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, embodiments, or drawings, should be understood to contemplate the possibilities of including one of the terms, either of the terms, or both terms. For example, the phrase "A or B" will be understood to include the possibilities of "A" or "B" or "A and B."

Although the present subject matter has been described herein in terms of certain embodiments, and certain exemplary methods, it is to be understood that the scope of the subject matter is not to be limited thereby. Instead, the Applicant intends that variations on the methods and materials disclosed herein which are apparent to those of skill in the art will fall within the scope of the disclosed subject matter.

What is claimed is:

1. A method for accessing a blood vessel with an over-the-needle guidewire, the method comprising:

puncturing the blood vessel with a needle having an over-the-needle portion of a guidewire disposed on the needle;

advancing the over-the-needle portion of the guidewire into the blood vessel while maintaining a position of the needle relative to the blood vessel, wherein the guidewire comprises a proximal portion, the over-the-needle portion, and a support wire, wherein the support wire is housed within a lumen in guidewire, the lumen extending through the proximal portion and the over-the-needle portion of the guidewire, and wherein the support wire extends from the proximal portion at least partially into the over-the-needle portion adjacent to the needle within the lumen of the guidewire when the needle is puncturing the blood vessel, the support wire configured to direct advancing forces on the guidewire along the needle while the over-the-needle portion of the guidewire is being advanced into the blood vessel; and withdrawing the needle from the over-the-needle portion of the guidewire while maintaining a position of the advanced guidewire relative to the blood vessel.

2. The method of claim 1, wherein the guidewire is pushed at an about 15degree angle relative to a longitudinal axis of the needle when the guidewire is being advanced into the blood vessel.

3. The method of claim 1, before puncturing the blood vessel with the needle, further comprising:

advancing the guidewire through a guidewire port of a luer, wherein the luer is connected to the needle to position the needle as desired relative to the blood vessel, and wherein the guidewire port is angled relative to a longitudinal axis of the needle, the guidewire port positioning the proximal portion of the guidewire at a predetermined angle relative to the longitudinal axis of the needle;

inserting the needle into an opening in the guidewire, the opening positioned on a middle portion of guidewire, the middle portion between the proximal portion and the over-the-needle portion of the guidewire, the opening in communication with the lumen of the guidewire; and advancing the needle adjacent the support wire into the lumen of the over-the-needle portion of the guidewire, and wherein while the over-the-needle portion of the guidewire is being advanced into the blood vessel, the proximal portion of the guidewire advances through the guidewire port and is maintained at the predetermined angle relative to the longitudinal axis of the needle.

4. The method of claim 1, further comprising:

advancing a dilator and a sheath over the guidewire into the blood vessel; and withdrawing the guidewire and the dilator while maintaining a position of the sheath within the blood vessel.

* * * * *